US009790523B2

(12) United States Patent
Tracy et al.

(10) Patent No.: US 9,790,523 B2
(45) Date of Patent: Oct. 17, 2017

(54) ENERGY EFFICIENT BATCH RECYCLE METHOD FOR THE PRODUCTION OF BIOMOLECULES

(71) Applicant: White Dog Labs, Inc., New Castle, DE (US)

(72) Inventors: Bryan P. Tracy, Wilmington, DE (US); Brian J. Waibel, Kennett Square, PA (US); Aharon M. Eyal, Jerusalem (IL)

(73) Assignee: WHITE DOG LABS, INC., New Castle, DE (US)

( * ) Notice: Subject to any disclaimer, the term of this patent is extended or adjusted under 35 U.S.C. 154(b) by 0 days.

(21) Appl. No.: 15/123,512

(22) PCT Filed: Feb. 25, 2015

(86) PCT No.: PCT/US2015/017465
§ 371 (c)(1),
(2) Date: Sep. 2, 2016

(87) PCT Pub. No.: WO2015/134246
PCT Pub. Date: Sep. 11, 2015

(65) Prior Publication Data
US 2017/0073707 A1 Mar. 16, 2017

Related U.S. Application Data

(60) Provisional application No. 61/947,997, filed on Mar. 4, 2014.

(51) Int. Cl.
| | |
|---|---|
| *C12P 7/16* | (2006.01) |
| *C07C 29/86* | (2006.01) |
| *A23K 10/12* | (2016.01) |
| *A23K 10/38* | (2016.01) |
| *A23K 10/14* | (2016.01) |

(52) U.S. Cl.
CPC .............. *C12P 7/16* (2013.01); *A23K 10/12* (2016.05); *A23K 10/14* (2016.05); *A23K 10/38* (2016.05); *C07C 29/86* (2013.01); *C12Y 301/03008* (2013.01); *Y02E 50/10* (2013.01); *Y02P 60/873* (2015.11)

(58) Field of Classification Search
CPC .......................... C12P 7/16; C12Y 301/03008
USPC ........................................................ 435/160
See application file for complete search history.

(56) References Cited

U.S. PATENT DOCUMENTS

| | | |
|---|---|---|
| 3,018,308 A | 1/1962 | Levine et al. |
| 3,950,442 A | 4/1976 | Vogel et al. |
| 4,409,406 A | 10/1983 | Feldman |
| 4,469,905 A | 9/1984 | Inwood et al. |
| 4,482,768 A | 11/1984 | Somekh |
| 4,508,928 A | 4/1985 | Victor |
| 4,761,505 A | 8/1988 | Diana et al. |
| 4,770,780 A | 9/1988 | Moses |
| 4,827,046 A | 5/1989 | Harandi et al. |
| 4,842,693 A | 6/1989 | Wheldon |
| 4,865,973 A | 9/1989 | Kollerup et al. |
| 4,877,530 A | 10/1989 | Moses |
| 4,956,052 A | 9/1990 | Hirata et al. |
| 4,981,491 A | 1/1991 | Harandi et al. |
| 5,009,859 A | 4/1991 | Harandi et al. |
| 5,036,005 A | 7/1991 | Tedder |
| 5,041,690 A | 8/1991 | Harandi et al. |
| 5,047,070 A | 9/1991 | Harandi et al. |
| 5,064,623 A | 11/1991 | Harandi et al. |
| 5,130,101 A | 7/1992 | Harandi et al. |
| 5,144,085 A | 9/1992 | Harandi et al. |
| 5,160,044 A | 11/1992 | Tan |
| 5,167,937 A | 12/1992 | Harandi et al. |
| 5,215,902 A | 6/1993 | Tedder |
| 5,332,478 A | 7/1994 | Berg |
| 5,338,411 A | 8/1994 | Berg |
| 5,387,721 A | 2/1995 | Kruse et al. |
| 5,437,770 A | 8/1995 | Berg |
| 5,445,716 A | 8/1995 | Berg |
| 5,447,608 A | 9/1995 | Berg |
| 5,453,166 A | 9/1995 | Berg |
| 5,563,301 A | 10/1996 | Preston et al. |
| 5,576,464 A | 11/1996 | Preston |
| 5,609,734 A | 3/1997 | Streicher et al. |
| 5,663,454 A | 9/1997 | Preston |
| 5,723,024 A | 3/1998 | Berg |
| 5,738,764 A | 4/1998 | Berg |
| 5,763,693 A | 6/1998 | Hirata et al. |

(Continued)

FOREIGN PATENT DOCUMENTS

| | | |
|---|---|---|
| GB | 627769 | 4/1949 |
| WO | 2004/055134 | 7/2004 |

(Continued)

OTHER PUBLICATIONS

Munson et al., "Factors Influencing Solvent Selection for Extraction of Ethanol from Aqueous Solutions," *Ind. Eng. Chem. Process Des. Dev.*, vol. 23, No. 1, pp. 109-115, 1984 (Abstract).

Mehta et al., "A Novel Extraction Process for Separating Ethanol and Water", *Ind. Eng. Chem. Process Des. Dev.*, vol. 24, pp. 556-560, 1985.

Krukonis et al., Supercritical Fluid Extraction, 2nd Ed., Butterworth-Heinemann, Figure 8.11, p. 173, 1994.

"CRC Handbook of Solubility Parameters and Other Cohesion Parameters", Second Edition, pp. 122-138, 1991.

(Continued)

*Primary Examiner* — Tekchand Saidha
(74) *Attorney, Agent, or Firm* — Greenblum & Berstein, P.L.C.

(57) ABSTRACT

Provided are methods, systems and apparatuses to the energy efficient and selective extraction of biomolecules, e.g., small organic compounds, e.g., one or more C3-C9 alcohols, one or more C3-C5 carboxylic acids, and mixtures thereof, from an aqueous solution, particularly aqueous solutions containing the alcohol in dilute or low concentrations, for example, fermentation broths.

20 Claims, 1 Drawing Sheet

(56) References Cited

U.S. PATENT DOCUMENTS

| | | |
|---|---|---|
| 5,763,694 A | 6/1998 | Berg |
| 5,763,695 A | 6/1998 | Berg |
| 5,776,321 A | 7/1998 | Berg |
| 5,808,161 A | 9/1998 | Brown et al. |
| 5,856,588 A | 1/1999 | Dai et al. |
| 5,876,569 A | 3/1999 | Berg |
| 5,897,750 A | 4/1999 | Berg |
| 5,904,815 A | 5/1999 | Berg |
| 5,993,610 A | 11/1999 | Berg |
| 6,024,841 A | 2/2000 | Berg |
| 6,039,846 A | 3/2000 | Berg |
| 6,211,390 B1 | 4/2001 | Peter et al. |
| 6,426,327 B1 | 7/2002 | Flynn et al. |
| 6,518,465 B2 | 2/2003 | Hoyme et al. |
| 7,427,684 B2 | 9/2008 | Crabtree et al. |
| 7,534,908 B2 | 5/2009 | Sorger et al. |
| 8,048,655 B2 | 11/2011 | Verser et al. |
| 8,088,958 B2 | 1/2012 | Schucker |
| 8,101,808 B2 | 1/2012 | Evanko et al. |
| 8,143,034 B2 | 3/2012 | Gross et al. |
| 8,263,814 B2 | 9/2012 | Waibel et al. |
| 8,354,563 B2 | 1/2013 | Kharas |
| 2009/0291481 A1 | 11/2009 | Hillyer |
| 2009/0314992 A1 | 12/2009 | Pinkos et al. |
| 2010/0041919 A1 | 2/2010 | Wu et al. |
| 2010/0069686 A1 | 3/2010 | Waibel et al. |
| 2010/0130761 A1 | 5/2010 | Boam et al. |
| 2010/0151098 A1 | 6/2010 | Catchpole et al. |
| 2011/0136193 A1 | 6/2011 | Grady et al. |
| 2011/0294181 A1 | 12/2011 | Weydahl |
| 2012/0277463 A1 | 11/2012 | Warner et al. |
| 2013/0001061 A1 | 1/2013 | Grady et al. |
| 2013/0096326 A1 | 4/2013 | Peterson et al. |
| 2013/0165670 A1 | 6/2013 | Allen et al. |
| 2014/0066669 A1 | 3/2014 | Schonemann et al. |
| 2014/0303408 A1 | 10/2014 | Zaher |

FOREIGN PATENT DOCUMENTS

| | | |
|---|---|---|
| WO | 2012/054400 | 4/2012 |
| WO | 2014/144643 | 9/2014 |

OTHER PUBLICATIONS

"Perry's Chemical Engineeting Handbook", 8th Edition, Chapter 15, 2008.

Treybal, "Liquid Extraction", First Edition, McGraw-Hill, New York, 1951.

Sun et al., "Anaerobic Methyl tert-Butyl Ether-Degrading Microorganisms Identified in Wastewater Treatment Plant Samples by Stable Isotope Probing," *Appl. Environ. Microbiol.*, vol. 78, No. 8, pp. 2973-2980, 2010.

Mahajani et al., "Reactive Distillation," *The Academic* Press, pp. 4075-4082, 2000.

"Acetobacterium," *Wikipedia*, http://en.wikipedia.org/wiki/Acetobacterium, retrieved on Feb. 13, 2014.

"Clostridium acetobutylicum," *Wikipedia*, http://en.wikipedia.org/wiki/Clostridium_acetobutylicum, retrieved on Feb. 13, 2014.

Daniel et al., "Utilization of Methoxylated Aromatic Compounds by the Acetogen *Clostridium thermmoaceticum*: Expression and Specificity of the Co-Dependent O-Demethylating Activity," *Biochem. Biophys. Res. Comm.*, vol. 180, No. 1, pp. 416-422, 1991.

Shuppert et al., "Fermentation of Methoxyacetate to Glycolate and Acetate by Newly Isolated Strains of *Acetobacterium* sp.," *Arch. Microbiol.*, vol. 153, pp. 200-204, 1990.

U.S. Appl. No. 61/947,997, filed Mar. 4, 2014.

"Experiment 3: Extraction: Separation of an Acidic, a Basic, and a Neutral Substance," 2013.

Extraction, 2011.

International Search Report for PCT/US2015/017465, dated May 20, 2015.

International Preliminary Report on Patentability for PCT/US2015/017465, dated Sep. 15, 2016.

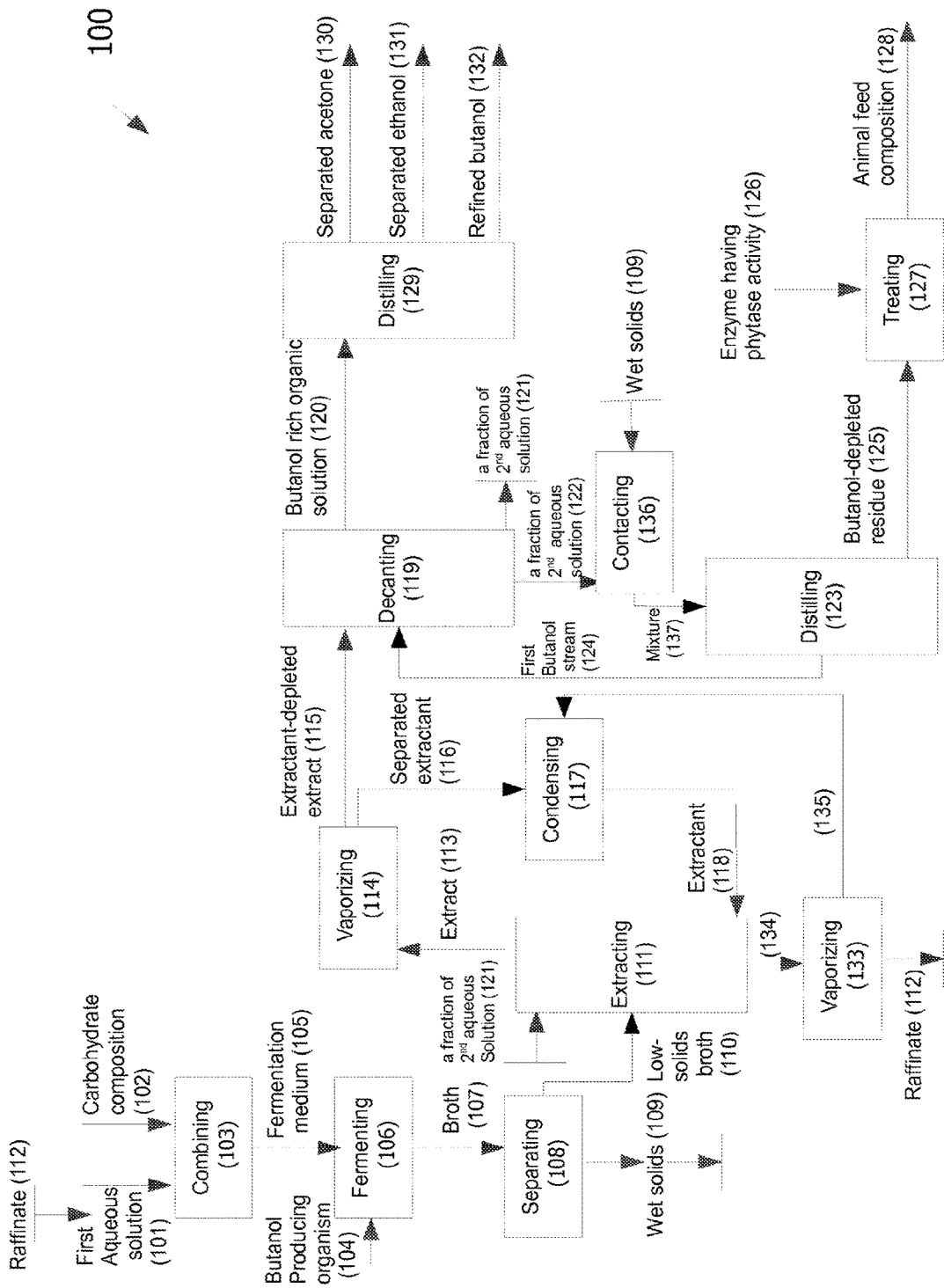

ENERGY EFFICIENT BATCH RECYCLE METHOD FOR THE PRODUCTION OF BIOMOLECULES

CROSS-REFERENCE TO RELATED APPLICATIONS

The instant application is the National Stage of International Application PCT/US2015/017465, filed Feb. 25, 2015, which claims priority on U.S. Provisional Application No. 61/947,977, filed Mar. 4, 2014, the disclosures each of which are hereby expressly incorporated by reference herein in their entireties.

FIELD

Provided are methods, systems and apparatuses to the energy efficient and selective extraction of biomolecules, e.g., small organic compounds, e.g., one or more C3-C9 alcohols, one or more C3-C5 carboxylic acids, and mixtures thereof, from an aqueous solution, particularly aqueous solutions containing the alcohol in dilute or low concentrations, for example, fermentation broths.

BACKGROUND

The notion of using a liquid solvent to extract lower alcohols, e.g., ethanol, from an aqueous solution has been pursued since the early 1980s. For example, in 1984, Munson and King published "Factors Influencing Solvent Selection for Extraction of Ethanol from Aqueous Solutions," Industrial and Engineering Chemistry Process Design and Development, 23, p 109-115. Munson and King examined solvents and solvent mixtures for the extraction of ethanol from dilute aqueous solutions. Results were tabulated on the basis of capacity, as represented by the distribution coefficient, and selectivity, as represented by the separation factor. Munson and King showed that an increasing distribution coefficient generally correlates with a decreasing separation factor. Thus, as the solvent become more effective for extracting ethanol, the solvent, unfortunately, becomes less effective for rejecting the water.

Previously disclosed methods of using an oil to extract ethanol from a dilute aqueous solution have proven to be energetically and economically inefficient. For example, Metha and Fraser, "A Novel Extraction Process for Separating Ethanol and Water," Industrial and Engineering Chemistry Process Design and Development, 24, 1985, p 556-560 detail a method to use light paraffin oil to extract ethanol from water. Their method leverages the ternary phase behavior of ethanol-water-paraffin oil system. The proposed process scheme requires process temperatures in the range from 30° C. to 115° C. The report does not provide the optimum process conditions. Ethanol's boiling point is 78° C. Furthermore, in order to have favorable energy input into the process, the process requires that paraffin oil travel with the discharged ethanol. Because paraffin oil is more valuable than ethanol, it is not clear that the proposed process has an economic advantage.

Numerous published methods for the extraction of ethanol require a distillation step to remove ethanol from water, which is energetically and economically inefficient, and an unnecessary additional step. For example, U.S. Pat. Nos. 4,409,406; 4,865,973; 4,770,780; 5,036,005; and 5,215,902 each disclose processes for the extraction of ethanol that require a distillation step to remove ethanol from water.

Others have also proposed using carbon dioxide as a primary extractant of ethanol from an aqueous solution. However, these methods are limited by the distribution coefficient between ethanol-water and $CO_2$ that has been measured to be on the order of 0.1 by numerous researchers, e.g., Krukonis (FIG. 8.11, p. 173, McHugh, M., Krukonis, V., Supercritical Fluid Extraction, 2nd Ed., Butterworth-Heinemann, 1994). These processes have no energy advantage over a traditional binary distillation process. See, for example, U.S. Pat. Nos. 4,842,693; 5,160,044; and 4,770,780.

SUMMARY

In one aspect, provided is a method for producing butanol. In some embodiments, the methods comprise:

(i) combining a carbon source with a first aqueous solution comprising at least one carboxylic acid, a carbon source, a nitrogen source and extractant to form a fermentation medium;

(ii) fermenting said medium with a butanol producing organism to form a broth comprising butanol, said carboxylic acid, a carbon source, a nitrogen source and extractant;

(iii) contacting said broth with an extractant to form an extract and a raffinate, wherein said extract comprises said extractant, butanol and water and wherein said raffinate comprises said carboxylic acid, a carbon source, a nitrogen source and extractant;

(iv) separating said extract from said raffinate;

(v) separating extractant from at least a fraction of said extract to form separated extractant and extractant-depleted extract;

(vi) separating butanol from at least a fraction of said extractant-depleted extract to form a first butanol stream; and (vii) repeating steps (i) to (vi), wherein said first aqueous solution comprises said raffinate and wherein said separated extractant is used in said contacting;

wherein a. extractant boiling point at atmospheric pressure is under 20° C.;

b. extractant Hansen solubility parameter polarity component is in the range between 2 $MPa^{0.5}$ and 8 $MPa^{0.5}$;

c. extractant Hansen solubility parameter H-bond component is in the range between 2 $MPa^{0.5}$ and 8 $MPa^{0.5}$; and d. extractant to broth ratio in said contacting is selected so that the formed extract comprises at least 51% of the butanol in the broth. In varying embodiments, said extractant-depleted extract comprises a butanol-rich organic solution and a butanol-comprising second aqueous solution. In varying embodiments, the methods further comprise separating butanol from at least a fraction of said second aqueous solution to form a first butanol stream and a butanol-depleted residue. In varying embodiments, said butanol is selected from a group consisting of n-butanol, iso-butanol and sec-butanol. In varying embodiments, said butanol is selected from a group consisting of n-butanol and iso-butanol. In varying embodiments, said carbon source comprises liquefied corn, further comprising separating wet solids from said broth prior to said contacting. In varying embodiments, said extractant-depleted extract comprises a butanol-rich organic solution and a butanol comprising second aqueous solution, comprising contacting said separated wet solids with a fraction of said second aqueous solution to form a mixture and separating butanol from said mixture to form butanol-depleted residue. In varying embodiments, said organism is viable in a broth comprising extractant at a concentration of at least about 1.0 g/L. In varying embodiments, said organism is a *Firmicutes*. In varying embodiments, said organism is a *Clostridia*. In varying embodiments, said organism is a *Eubacterium*. In varying embodiments, the *Eubacterium* is a *Eubacterium limosum*. In varying embodiments, said organism is a *Clostridium*. In varying embodiments, said organism is a *Clostridium* selected from the group consisting of *Clostridium butyricum, Clostridium acetobutylicum, Clostridium saccharoperbutylacetonicum, Clostridium beijerickii, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum* and *Clostridium autoethanogenum*. In varying embodiments, said fermentation medium is inoculated with said organism. In varying embodiments, said broth comprises carbon source at a concentration greater than about 1 g/L. In varying embodiments, said carboxylic acid is selected from the group consisting of acetic acid, butyric acid and lactic acid. In varying embodiments, said extract comprises less than 10% of the carboxylic acid in said broth. In varying embodiments, the methods further comprise maintaining the pH of the broth above about pH 6 during contacting with the extractant. In varying embodiments, said extractant is selected from the group consisting of dimethyl ether (DME), methyl ethyl ether, and mixtures thereof. In varying embodiments, the methods further comprise distilling said butanol-rich organic solution to form refined butanol. In varying embodiments, said broth comprises ethanol, comprising distilling said butanol-rich organic solution to form refined butanol and separated ethanol. In varying embodiments, said broth comprises acetone, comprising distilling said butanol-rich organic solution to form refined butanol and separated acetone. In varying embodiments, at least a fraction of said second aqueous solution is contacted with at least a fraction of said extract to form a butanol-depleted solution and a butanol enriched extract. In varying embodiments, said first aqueous solution comprises at least 0.1 wt. % of said extractant. In varying embodiments, said broth comprises ethanol and wherein the extractant to broth ratio in said contacting is selected so that the fraction of the broth butanol in said extract is greater than the fraction of the broth ethanol in said extract. In varying embodiments, said broth comprises acetone and wherein the extractant to broth ratio in said contacting is selected so that the fraction of the broth butanol in said extract is greater than the fraction of the broth acetone in said extract. In varying embodiments, said fermentation medium comprises ethanol at a concentration greater than about 0.1 g/L. In varying embodiments, said fermentation medium does not comprise acetone. In varying embodiments, said fermentation medium comprises acetone at a concentration greater than about 0.1 g/L. In varying embodiments, said fermentation medium comprises said carboxylic acid at a concentration greater than about 0.1 g/L. In varying embodiments, said separating extractant comprises vaporizing, said using said separated extractant in said contacting comprises condensing and wherein said vaporizing and said condensing are driven by a refrigerant circuit. In varying embodiments, the butanol-rich organic solution and a butanol-comprising second aqueous solution are in separable phases, wherein biomolecules having a distribution coefficient in the extractant that is greater than one concentrate in the butanol-rich organic solution and biomolecules having a distribution coefficient in the extractant that is less than one concentrate in the second aqueous solution.

In varying embodiments, the methods further comprise separating the butanol-rich organic solution and the butanol-comprising second aqueous solution and combining the butanol-comprising second aqueous solution with the first aqueous solution.

In a further aspect, provided is a method for production of butanol. In some embodiments, the methods comprise:

(i) fermenting a fermentation medium with a butanol-producing organism to form a broth comprising butanol, a coproduct selected from a group consisting of ethanol, acetone and combinations thereof, and at least one carboxylic acid;

(ii) contacting said broth with an extractant to form an extract and a raffinate, wherein said extract comprises said extractant, butanol, water and said coproduct and wherein said raffinate comprises said carboxylic acid;

(iii) maintaining the pH of said broth above about pH 6 during said contacting with said extractant;

(iv) separating said extract from said raffinate;

(v) separating extractant from at least a fraction of said extract to form separated extractant, a butanol-rich organic solution comprising said coproduct, and a butanol-comprising second aqueous solution; and (vi) distilling said butanol-rich organic solution to form refined butanol and separated coproduct;

wherein a. extractant boiling point at atmospheric pressure is under 20° C.;

b. extractant Hansen solubility parameter polarity component is in the range between 2 $MPa^{0.5}$ and 8 $MPa^{0.5}$;

c. extractant Hansen solubility parameter H-bond component is in the range between 2 $MPa^{0.5}$ and 8 $MPa^{0.5}$; and d. extractant to broth ratio in said contacting is selected so that the formed extract comprises at least 51% of the butanol in the broth. In varying embodiments, the methods further comprise contacting a fraction of said second aqueous solution with at least a fraction of said extract to form a butanol enriched extract and a butanol-depleted solution. In varying embodiments, said butanol is selected from a group consisting of n-butanol, iso-butanol and sec-butanol. In varying embodiments, said butanol is selected from a group consisting of n-butanol and iso-butanol. In varying embodiments, said organism is viable in a broth comprising extractant at a concentration of at least about 1.0 g/L. In varying embodiments, said organism is a *Firmicutes*. In varying embodiments, said organism is a *Clostridia*. In varying embodiments, said organism is a *Eubacterium*. In varying embodiments, the *Eubacterium* is a *Eubacterium limosum*. In varying embodiments, said organism is a *Clostridium*. In varying embodiments, said organism is a *Clostridium* selected from the group consisting of *Clostridium butyricum, Clostridium acetobutylicum, Clostridium saccharoperbutylacetonicum, Clostridium beijerickii, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum* and *Clostridium autoethanogenum*. In varying embodiments, said fermentation medium is inoculated with said organism. In varying embodiments, said carboxylic acid is selected from a group consisting of acetic acid, butyric acid and lactic acid. In varying embodiments, said extract comprises less than 10% of the carboxylic acid in said broth. In varying embodiments, said extractant is selected from the group consisting of dimethyl ether (DME), methyl ethyl ether, and mixtures thereof. In varying embodiments, said fermentation medium comprises liquefied corn and wherein said broth comprises solids, comprising separating wet solids from said broth prior to said contacting. In varying embodiments, the methods further comprise contacting at least a fraction of said second aqueous solution with said separated wet solids to form a mixture and separating butanol from said mixture to form a butanol-depleted residue and a first butanol stream. In varying embodiments, said coproduct is ethanol and wherein the extractant to broth ratio in said contacting is selected so that the fraction of the broth butanol in said extract is greater than the fraction of the broth ethanol in said extract. In varying embodiments, said coproduct is acetone and wherein the extractant to broth ratio in said contacting is selected so that the fraction of the broth butanol in said extract is greater than the fraction of the broth acetone in said extract. In varying embodiments, said fermentation medium comprises ethanol at a concentration greater than about 0.1 g/L. In varying embodiments, said fermentation medium does not comprise acetone. In varying embodiments, said fermentation medium comprises acetone at a concentration greater than about 0.1 g/L. In varying embodiments, said fermentation medium comprises said carboxylic acid at a concentration greater than about 0.1 g/L. In varying embodiments, fermentation medium comprises at least 0.1 wt. % of said extractant. In varying embodiments, said separating extractant comprises vaporizing, said contacting comprises condensing and wherein said vaporizing and said condensing are driven by a refrigerant circuit. In varying embodiments, the methods further comprise forming a fermentation medium comprising said raffinate. In varying embodiments, the raffinate is added to the fermentation medium without prior sterilization.

In a further aspect, provided is a method for production of butanol. In some embodiments, the methods comprise:

(i) fermenting a fermentation medium comprising liquefied corn with a butanol producing organism to form a broth comprising butanol, a coproduct selected from a group consisting of ethanol, acetone and combinations thereof, at least one carboxylic acid and solids;

(ii) separating wet solids from said broth to form a low-solids broth;

(iii) contacting said low-solids broth with an extractant to form an extract and a raffinate, wherein said extract comprises said extractant, butanol, water and said coproduct and wherein said raffinate comprises said carboxylic acid;

(iv) separating said extract from said raffinate;

(v) separating extractant from at least a fraction of said extract to form separated extractant, a butanol-rich organic solution comprising said coproduct, and butanol comprising second aqueous solution;

(vi) contacting at least a fraction of said second aqueous solution with said separated wet solids to form a mixture and separating butanol from said mixture to form a butanol-depleted residue and a first butanol stream; and (vii) distilling said butanol-rich organic solution to form refined butanol and separated coproduct;

wherein a. extractant boiling point at atmospheric pressure is under 20° C.;

b. extractant Hansen solubility parameter polarity component is in the range between 2 $MPa^{0.5}$ and 8 $MPa^{0.5}$; and c. extractant Hansen solubility parameter H-bond component is in the range between 2 $MPa^{0.5}$ and 8 $MPa^{0.5}$; and d. extractant to broth ratio in said contacting is selected so that the formed extract comprises at least 51% of the butanol in the broth. In varying embodiments, the methods further comprise maintaining the pH of the low-solids broth above about pH 6 during contacting with the extractant. In varying embodiments, the methods further comprise contacting another fraction of said second aqueous phase solution with at least a fraction of said extract to form a butanol-enriched extract and a butanol-depleted solution. In varying embodiments, said butanol is selected from a group consisting of n-butanol, iso-butanol and sec-butanol. In varying embodiments, said butanol is selected from a group consisting of n-butanol and iso-butanol. In varying embodiments, said organism is viable in a broth comprising extractant at a concentration of at least about 1.0 g/L. In varying embodiments, said organism is a *Firmicutes*. In varying embodiments, said organism is a *Clostridia*. In varying embodiments, said organism is a *Eubacterium*. In varying embodiments, the *Eubacterium* is a *Eubacterium limosum*. In varying embodiments, said organism is a *Clostridium*. In varying embodiments, said organism is a *Clostridium* selected from the group consisting of *Clostridium butyricum, Clostridium acetobutylicum, Clostridium saccharoperbutylacetonicum, Clostridium beijerickii, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum* and *Clostridium autoethanogenum*. In varying embodiments, said fermentation medium is inoculated with said organism. In varying embodiments, said carboxylic acid is selected from a group consisting of acetic acid, butyric acid and lactic acid. In varying embodiments, said extract comprises less than 10% of the carboxylic acid in said broth. In varying embodiments, said extractant is selected from the group consisting of dimethyl ether (DME), methyl ethyl ether, and mixtures thereof. In varying embodiments, said coproduct is ethanol and wherein the extractant to broth ratio in said contacting is selected so that the fraction of the broth butanol in said extract is greater than the fraction of the broth ethanol in said extract. In varying embodiments, said coproduct is acetone and wherein the extractant to broth ratio in said contacting is selected so that the fraction of the broth butanol in said extract is greater than the fraction of the broth acetone in said extract. In varying embodiments, said fermentation medium comprises ethanol at a concentration greater than about 0.1 g/L. In varying embodiments, said fermentation medium does not comprise acetone. In varying embodiments, said fermentation medium comprises acetone at a concentration greater than about 0.1 g/L. In varying embodiments, said fermentation medium comprises said carboxylic acid at a concentration greater than about 0.1 g/L. In varying embodiments, the fermentation medium comprises at least 0.1 wt. % of said extractant. In varying embodiments, said separating extractant comprises vaporizing, said contacting comprises condensing and wherein said vaporizing and said condensing are driven by a refrigerant circuit. In varying embodiments, the methods further comprise forming a fermentation medium comprising said raffinate. In varying embodiments, the raffinate is added to the fermentation medium without prior sterilization.

In another aspect, provided is a method for the production of butanol. In some embodiments, the methods comprise:

(i) fermenting a medium comprising a carbon source and a nitrogen source with a butanol producing organism that is viable in a broth comprising a concentration of at least about 1.0 g/L extractant to form a broth comprising butanol and at least one carboxylic acid;

(ii) maintaining the pH of said broth at a pH above about 6;

(iii) contacting said broth with an extractant to form an aqueous raffinate comprising said carboxylic acid and an extract comprising butanol and water;

(iv) separating extractant from at least a fraction of said extract to form separated extractant, a butanol-rich organic phase and butanol-comprising second aqueous phase; and (v) distilling said butanol-rich organic phase to form refined butanol wherein a. extractant boiling point at atmospheric pressure is under 20° C.;

b. extractant Hansen solubility parameter polarity component is in the range between 2 $MPa^{0.5}$ and 8 $MPa^{0.5}$; and c. extractant Hansen solubility parameter H-bond component is in the range between 2 $MPa^{0.5}$ and 8 $MPa^{0.5}$. In varying embodiments, said broth comprises ethanol, wherein said organic phase comprises ethanol and wherein said distilling said butanol-rich organic phase further forms separated ethanol. In varying embodiments, said broth comprises acetone, wherein said organic phase comprises acetone and wherein said distilling said butanol-rich organic phase further forms separated acetone. In varying embodiments, said organism is modified to eliminate ethanol production. In varying embodiments, said organism is modified to eliminate acetone production. In varying embodiments, said organism is a *Firmicutes*. In varying embodiments, said organism is a *Clostridia*. In varying embodiments, said organism is a *Eubacterium*. In varying embodiments, the *Eubacterium* is a *Eubacterium limosum*. In varying embodiments, said organism is a *Clostridium*. In varying embodiments, said organism is a *Clostridium* selected from the group consisting of *Clostridium butyricum*, *Clostridium acetobutylicum*, *Clostridium saccharoperbutylacetonicum*, *Clostridium beijerickii*, *Clostridium saccharobutylicum*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum* and *Clostridium autoethanogenum*.

In another aspect, provided is a butanol composition comprising at least 40 wt. % butanol and at least 100 ppb extractant, wherein the extractant is selected from the group consisting of dimethyl ether (DME), methyl ethyl ether, and mixtures thereof.

In a further aspect, provided is a method for producing a fermentation product and at least one fermentation coproduct. In some embodiments, the methods comprise:

(i) combining a carbon source with a first aqueous solution comprising a fermentation coproduct and extractant to form a fermentation medium;

(ii) fermenting said medium with an organism to form a broth comprising a product, said coproduct, and extractant;

(iii) contacting said broth with an extractant to form an extract and a raffinate, wherein said extract comprises said extractant, said product and water and wherein said raffinate comprises said coproduct and extractant;

(iv) separating said extract from said raffinate;

(v) separating extractant from at least a fraction of said extract to form separated extractant and extractant-depleted extract;

(vi) separating product from at least a fraction of said extractant-depleted extract to form a product stream; and (vii) repeating steps (i) to (vi), wherein said first aqueous solution comprises said raffinate and wherein said separated extractant is used in said contacting;

wherein a. extractant boiling point at atmospheric pressure is under 20° C.;

b. extractant Hansen solubility parameter polarity component is in the range between 2 $MPa^{0.5}$ and 8 $MPa^{0.5}$;

c. extractant Hansen solubility parameter H-bond component is in the range between 2 $MPa^{0.5}$ and 8 $MPa^{0.5}$;

d. extractant to broth ratio in said contacting is selected so that the formed extract comprises at least 51% of the butanol in the broth; and e. said coproduct is selected from a group consisting of carboxylic acids and biomolecules characterized by solubility parameter greater than that of said product. In varying embodiments, said first aqueous solution comprises at least one of a carboxylic acid, a carbon source and a nitrogen source. In varying embodiments, said broth comprises at least one of a carboxylic acid, a carbon source and a nitrogen source. In varying embodiments, said raffinate comprises at least one of a carboxylic acid, a carbon source and a nitrogen source. In varying embodiments, said extract comprises said coproduct. In varying embodiments, said extractant-depleted extract comprises a product-rich organic solution and a product comprising second aqueous solution. In varying embodiments, the methods further comprise separating product from at least a fraction of said second aqueous solution to form a first product stream and a product-depleted residue. In varying embodiments, said carbon source comprises liquefied corn, and further comprising separating wet solids from said broth prior to said contacting. In varying embodiments, said extractant-depleted extract comprises a product rich organic solution and a product comprising second aqueous solution, comprising contacting said separated wet solids with a fraction of said second aqueous solution to form a mixture and separating product from said mixture to form product-depleted residue. In varying embodiments, said organism is viable in a broth comprising extractant at a concentration of at least about 1.0 g/L. In varying embodiments, said organism is a *Firmicutes*. In varying embodiments, said organism is a *Clostridia*. In varying embodiments, said organism is a *Eubacterium*. In varying embodiments, the *Eubacterium* is a *Eubacterium limosum*. In varying embodiments, said organism is a *Clostridium*. In varying embodiments, said organism is a *Clostridium* selected from the group consisting of *Clostridium butyricum*, *Clostridium acetobutylicum*, *Clostridium saccharoperbutylacetonicum*, *Clostridium beijerickii*, *Clostridium saccharobutylicum*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum* and *Clostridium autoethanogenum*. In varying embodiments, said fermentation medium is inoculated with said organism. In varying embodiments, said carboxylic acid is selected from a group consisting of acetic acid, butyric acid and lactic acid. In varying embodiments, the methods further comprise maintaining the pH of the broth above about pH 6 during contacting with the extractant. In varying embodiments, said extractant is selected from the group consisting of dimethyl ether (DME), methyl ethyl ether, and mixtures thereof. In varying embodiments, at least a fraction of said second aqueous solution is contacted with at least a fraction of said extract to form a product-depleted solution and a product-enriched extract. In varying embodiments, said first aqueous solution comprises at least 0.1 wt. % of said extractant. In varying embodiments, the extractant to broth ratio in said contacting is selected so that the fraction of the broth product in said extract is greater than the fraction of the broth coproduct in said extract. In varying embodiments, said fermentation medium comprises coproduct at a concentration greater than about 0.1 g/L. In varying embodiments, said fermentation medium comprises carboxylic acid at a concentration greater than about 0.1 g/L. In varying embodiments, said separating extractant comprises vaporizing, said using said separated extractant in said contacting comprises condensing and wherein said vaporizing and said condensing are driven by a refrigerant circuit. In varying embodiments, said product is butanol. In varying embodiments, said coproduct is selected from a group consisting of ethanol, acetone, a carboxylic acid and their combinations. In varying embodiments, the methods further comprise distilling said product rich organic solution to form refined butanol. In varying embodiments, said extract comprises said coproduct and wherein said coproduct comprises ethanol, comprising distilling said product rich organic solution to form refined butanol and separated ethanol. In varying embodiments, said extract comprises said coproduct and wherein said coproduct comprises acetone, comprising distilling said product rich organic solution to form refined butanol and separated ethanol. In varying embodiments, said extract comprises said coproduct and wherein said coproduct comprises ethanol and acetone, comprising distilling said product rich organic solution to form refined butanol, separated ethanol and separated acetone. In varying embodiments, said product is propionic acid and wherein said coproduct is acetic acid. In varying embodiments, the methods further comprise maintaining the pH of the broth below about pH 5 during contacting with the extractant. In varying embodiments, said coproduct is assimilated to at least one of ethanol, acetone and butanol. In varying embodiments, said product is gamma-butyrolactone and wherein said coproduct is 1,4-butanediol. In varying embodiments, said product is butanol and wherein said coproduct is iso-propanol. In varying embodiments, said product is hexanol and wherein said coproduct is acetic acid. In varying embodiments, said coproduct is acetic acid. In varying embodiments, said product or co-product comprises one or more C3-C9 alcohols. In varying embodiments, the one or more C3-C9 alcohols are selected from a propanol, a butanol, a pentanol, a hexanol, a heptanol, an octanol and a nonanol. In varying embodiments, the alcohol comprises a propanol. In varying embodiments, the propanol is selected from the group consisting of 1-propanol and 2-propanol. In varying embodiments, the alcohol comprises a butanol. In varying embodiments, the butanol is selected from the group consisting of 1-butanol, 2-butanol, tert-butanol (2-methyl-2-propanol), and iso-butanol (2-methyl-1-propanol). In varying embodiments, the alcohol comprises a pentanol. In varying embodiments, the pentanol is selected from the group consisting of 1-pentanol, 2-pentanol, 3-pentanol, 2-methyl-1-butanol, 3-methyl-1-butanol, 2-methyl-2-butanol, 3-methyl-2-butanol, and 2,2-dimethyl-1-propanol. In varying embodiments, the alcohol comprises a hexanol. In varying embodiments, the hexanol is selected from the group consisting of 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, and 2 ethyl-1-butanol. In varying embodiments, the alcohol comprises a heptanol. In varying embodiments, the heptanol is selected from the group consisting of 1-heptanol, 2-heptanol, 3-heptanol and 4-heptanol. In varying embodiments, the alcohol comprises an octanol. In varying embodiments, the octanol is selected from the group consisting of 1-octanol and 2-ethylhexanol. In varying embodiments, the alcohol comprises a nonanol. In varying embodiments, the nonanol is selected from 1 nonanol, 2-nonanol, 3-nonanol, 4-nonanol and 5-nonanol. In varying embodiments, the product or co-product comprises one or more biomolecules selected from acetic acid, C3-C5 carboxylic acids, C3 C5 dicarboxylic acids, C3-C18 dicarboxylic acids, C8-C18 fatty alcohols, gamma-butyrolactone, butanediols, butadienes, furfurals, furan and acetoin. In varying embodiments, the biomolecule comprises one or more C3-C5 carboxylic acids or dicarboxylic acids. In varying embodiments, the one or more C3-C5 carboxylic acids or dicarboxylic acids are selected from the group consisting of propionic acid, lactic acid, malonic acid, fumaric acid, succinic acid, itaconic acid, levulinic acid and 3 hydroxybutyric acid. In varying embodiments, the biomolecule comprises one or more C2-C18 dicarboxylic acids. In varying embodiments, the one or more C3-C18 dicarboxylic acids are selected from the group consisting of oxalic, propanedioic, butanedioic, pentanedioic, hexanedioic, heptanedioic, octanedioic, nonanedioic, decanedioic, undecanedioic, and dodecanedioic (DDDA). In varying embodiments, the product comprises one or more carboxylic acids or dicarboxylic acids and the pH of the broth is maintained during contacting with the extractant at a pH below about 5. In varying embodiments, the co-product comprises one or more carboxylic acids or dicarboxylic acids and the pH of the broth is maintained during contacting with the extractant at a pH above about 6. In varying embodiments, the biomolecule comprises one or more C8-C18 fatty alcohols. In varying embodiments, the one or more C8-C18 fatty alcohols are selected from the group consisting of capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol) and stearyl alcohol (1-octadecanol). In varying embodiments, the biomolecule comprises one or more butanediols. In varying embodiments, the one or more butanediols are selected from 1,4 butanediol and 2,3-butanediol. In varying embodiments, the biomolecule comprises one or more butadienes. In varying embodiments, the one or more butadienes are selected from the group consisting of butadiene and 2-methyl-1,3-butadiene (isoprene). In varying embodiments, the biomolecule comprises one or more furfurals. In varying embodiments, the one or more furfurals are selected from the group consisting of furfural and hydroxymethylfurfural (5 (hydroxymethyl)-2-furalaldehyde). In varying embodiments, the biomolecule comprises acetoin and/or furan. In varying embodiments, said product has a solubility in water of less than about 15 wt. % at 25° C. In varying embodiments, said product has a carbon atom number to hydroxyl group ratio of 3 or greater. In varying embodiments, said product has a melting point of 100° C. or less. In varying embodiments, said coproduct comprises biomolecules characterized by solubility parameter greater than that of said product. In varying embodiments, the solubility parameter of said coproduct is greater than that of the product by at least about 0.5 MPa$^{0.5}$. In varying embodiments, the extractant-depleted extract comprises an organic phase and an aqueous phase, wherein biomolecules having a distribution coefficient in the extractant that is greater than one concentrate in the organic phase and biomolecules having a distribution coefficient in the extractant that is less than one concentrate in the aqueous phase. In varying embodiments, the methods further comprise separating the organic phase and the aqueous phase and combining the aqueous phase with the first aqueous solution.

In another aspect, provided are animal feed compositions comprising at least a fraction of said butanol-depleted residue as produced in the methods described above and herein. In another aspect, provided is a method for the production of such animal feed compositions, comprising treating said butanol-depleted residue with an enzyme having phytase activity.

Definitions

As used herein, the term "carbohydrate composition" refers to any composition comprising at least one carbohydrate, including aqueous solutions, solids and slurries, wherein the carbohydrates are selected from monomers, dimers, oligomers and polysaccharides and comprise pentoses, hexoses and their combinations.

As used herein, the term "carbon source" refers to any composition comprising at least one of a carbohydrate composition, glycerol and methanol.

As used herein, the term "nitrogen source" refers to compounds and compositions providing nitrogen to fermenting organisms, e.g. corn steep liquor and its components, yeast extract ammonia, ammonium salts and its components and other nitrogen compounds.

As used herein, the term "extractant" refers to an organic liquid with limited solubility in water.

As used herein, "contacting with extractant" "extraction" and "liquid-liquid extraction" interchangeably refer to contacting an aqueous solution or an aqueous slurry with an extractant, whereby a solute in the aqueous solution or slurry transfers (is extracted) to the extractant phase.

As used herein, the term "extract" refers to an extractant-rich phase generated during extraction, which phase comprises said extracted solute.

As used herein, the term "raffinate" refers to the solute-depleted aqueous solution or slurry generated during extraction.

As used herein, the term "extractant to broth ratio" and "phase ratio" interchangeably refer to the weight ratio between the extractant and the broth introduced into the extraction step. In a continuous operation, such as in counter-current extraction, the ratio is between the weight fluxes of the extractant and of the broth in terms of weight per unit time, e.g. tons per hour of extractant divided by tons per hour of broth, also referred to as "flux ratio" or as "extractant/broth flux ratio".

As used herein, the term "liquefied corn" refers to corn kernels treated with hot water and starch-hydrolyzing enzymes.

Hansen solubility parameter: Solubility parameter ($\delta$) was defined by Hildebrand as the square root of the cohesive energy density, which density is defined as the ratio between heat of vaporization and molar volume of the liquid. Hansen extended the original Hildebrand parameter to three-dimensional cohesion parameter. According to this concept, the total solubility parameter delta is separated into three different components, or, partial solubility parameters relating to the specific intermolecular interactions:

$$\delta 2 = \delta d^2 + \delta p^2 + \delta h^2$$

wherein $\delta d$, $\delta p$ and $\delta h$ are the dispersion, polarity, and hydrogen bonding components, respectively. Hoy proposed a system to estimate total and partial solubility parameters. The unit used for those parameters is MPa$^{1/2}$. A detailed explanation of that parameter and its components could be found in "CRC Handbook of Solubility Parameters and Other Cohesion Parameters", second edition, pages 122-138. That and other references provide tables with the parameters for many compounds. In addition, methods for calculating such parameters are provided.

As used herein, the term "distribution coefficient" refers to the ratio between the concentration of a solute in an organic phase and its concentration in an aqueous phase, while those phases are in equilibrium.

As used herein, the term "selectivity" refers to the ratio between distribution coefficients of two solutes. That selectivity determines, along with extraction parameters, the relative proportion of the two solutes in the extract. In the context of the methods described herein, butanol selectivity over water plays a key role. It is important to keep in mind that presence of additional components may strongly affect the selectivity. Hence, the butanol/water selectivity in extraction from a broth comprising ethanol and acetone would differ from that in extraction from a binary solution containing only water and butanol.

As used herein, the term "extraction yield" means the extent of extraction as calculated by dividing the amount of a solute in the extract by the combined amounts of that solute in the extract and raffinate.

As used herein, the term "carboxylic acid" refers to both free and salt form.

As used herein, the term "vaporizing" refers to transferring from a liquid phase into a vapor phase, e.g. by temperature elevation, pressure reduction, bubbling a gas and combinations thereof.

As used herein, the term "condensing" refers to transferring from a vapor phase to a liquid phase, e.g. by temperature reduction, pressure elevation and combinations thereof.

As used herein, the terms "fermentation" and "fermentation process" refer to a process in which a biocatalyst is cultivated in a culture medium containing raw materials, such as feedstock and nutrients, wherein the biocatalyst converts raw materials, such as a feedstock, into products.

As used herein, the term "fermentation medium" refers to a composition containing a carbon source (e.g., a carbohydrate), a nitrogen source and optionally other nutrients in which fermentation takes place.

As used herein, the term "fermentation broth" refers to the fermentation medium post fermentation, as such or after removal of biomass therefrom.

As used herein, the term "inhibition", when referring to an organism, refers to not restraining any portion of the life cycle or metabolic activity of the organism.

As used herein, the term "growth inhibition" refers to the inhibition of cell division. Cell division increases the cell population count.

As used herein, the term "solventogenesis inhibition" refers to inhibition of the cell's metabolic activity during the portion of the organism population's life cycle phase in which product and coproduct production is occurring.

As used herein, the terms "co-solvent" refers to a component affecting the mutual solubility of two other components. For example, on mixing about equal amounts of n-butanol and water at 25° C., two phases are formed: an aqueous phase containing about 7% butanol and a butanol phase containing about 20% water. Adding ethanol and re-equilibrating forms two phases so that in the aqueous phase the butanol/water ratio is greater than that in the binary system and a butanol phase where the water/butanol ratio is greater than that in the binary system.

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2%, the biocatalyst is tolerant to 2% of the inhibitor or has a tolerance to 2% of the inhibitor. The term "tolerance to temperature" is defined as the ability of the biocatalyst to maintain its specific productivity at a given temperature. The term "tolerance to extractant" is defined as the ability of the biocatalyst to maintain its specific productivity at a given concentration of extractant.

As used herein, the terms "coproduct" refers to a biomolecule generated during the fermentation concurrently with the product.

As used herein, the term "biomolecule" refers to any molecule generated by a living organism in the fermentation, which includes proteins, polysaccharides, lipids, nucleic acids, and primary or secondary metabolites.

Unless indicated otherwise, percent is weight percent and ratio is weight ratio.

BRIEF DESCRIPTION OF THE DRAWINGS

FIG. 1 illustrates an embodiment of the methods described herein.

DETAILED DESCRIPTION

1. Introduction

Methods are provided based, in part, on discoveries related to the production of butanol by fermentation with a butanol-producing organism producing at least one carboxylic acid and optionally, ethanol and/or acetone. According to one of the discoveries, the organism remains viable and its growth is not inhibited while fermenting in a fermentation medium originally containing relatively high concentrations of ethanol and acetone (at a particular ratio and concentration determined by extractant selectivity and flux ratio), carboxylic acid and extractant. This discovery enables the recycle of extraction raffinate to form fermentation medium, which increases the yield on carbon sources, nitrogen source and other nutrients. Surprisingly, the raffinate which has been exposed to extractant can be recycled to form a fermentation medium without prior or further sterilization. Furthermore, recycling of the raffinate saves on costs of removing residual extractant from the broth prior to recycling. It also saves on costs of extraction, where high yields of ethanol and acetone extraction are not required. It was further discovered that the organism assimilates carboxylic acid at this complex composition of fermentation medium. This discovery, combined with the ability to block extraction of carboxylic acid by pH adjustment, enables recycling carboxylic acid with the raffinate to be used as carbon source, which further increases the yield on carbon source. Another discovery is that the attainable butanol concentration in the broth (as determined by the specific fermentation medium and organism choice), combined with butanol over water selectivity (as determined by extractant properties and extraction parameters) are high enough—at the specific composition generated by raffinate recycle and by the selectivity of the particular extractant—to generate two phase in the extractant-depleted extract, even in the presence of the high proportions of ethanol and acetone, as dictated by the raffinate recycle (ethanol and acetone act as co-solvents, improving the mutual solubility of butanol and water). This split into two phases generates a butanol-rich organic phase, saving on costs of further refining and concentration of the product butanol.

2. Methods of Butanol Production a. Method of the First Aspect

According to a first aspect, provided is a method for producing butanol comprising (i) combining a carbon source with a first aqueous solution comprising at least one carboxylic acid, a carbon source (e.g., a carbohydrate), a nitrogen source and extractant to form a fermentation medium; (ii) fermenting said medium with a butanol producing organism to form a broth comprising butanol, said carboxylic acid, a carbon source, a nitrogen source and extractant; (iii) contacting said broth with an extractant to form an extract and a raffinate, wherein said extract comprises said extractant, butanol and water and wherein said raffinate comprises said carboxylic acid, a carbon source, a nitrogen source and extractant; (iv) separating said extract from said raffinate; (v) separating extractant from at least a fraction of said extract to form separated extractant and extractant-depleted extract; (vi) separating butanol from at least a fraction of said extractant-depleted extract to form a first butanol stream; and (vii) repeating steps (i) to (vi), wherein said first aqueous solution comprises said raffinate and wherein said separated extractant is used in said contacting; and wherein (a) extractant boiling point at atmospheric pressure is under 20° C.; (b) extractant Hansen solubility parameter polarity component is in the range between 2 $MPa^{0.5}$ and 8 $MPa^{0.5}$; (c) extractant Hansen solubility parameter H-bond component is in the range between 2 $MPa^{0.5}$ and 8 $MPa^{0.5}$; and (d) extractant to broth ratio in said contacting is selected so that the formed extract comprises at least about 40%, e.g., at least about 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, of the butanol in the broth.

i. Formation of Fermentation Medium

Any carbon source composition is suitable. In varying embodiments, the carbon source is a carbohydrate composition. According to an embodiment, said carbohydrate composition comprises at least one hexose, such as glucose and fructose. Alternatively or additionally, said carbohydrate composition comprises at least one pentose, such as xylose or arabinose. Alternatively or additionally, said carbohydrate composition comprises at least one of disaccharides, trisaccharides, oligosaccharides and polysaccharides. Examples include carbohydrate composition containing polysaccharides, such as starch, cellulose and hemicellulose, ones containing disaccharides, such as sucrose, sugarcane juice and sucrose-containing molasses, and monosaccharides, such as glucose and fructose. Suitable compositions include starchy crops, such as corn and wheat, sugarcane and sugar beet, molasses and lignocellulosic material. Suitable compositions also include algae and microalgae. Where desired, the compositions may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation.

According to an embodiment, said carbon source results from processing starch or a starch-comprising composition, e.g. corn kernels or wheat grains. According to an embodiment, said carbon source is liquefied corn. Alternatively or additionally, said carbon source results from processing cellulose or a cellulose-comprising composition.

According to the method of the first aspect, said carbon source is combined with a first aqueous solution comprising at least one carboxylic acid, a carbon source, a nitrogen source and extractant to form a fermentation medium. Any form of combining is suitable, e.g., mixing. Optionally, said carbon composition, said first aqueous solution or both is treated prior to combining, e.g., sterilized. Optionally, the product of combining is further treated, e.g., combined with additional nutrients. According to an embodiment, said first aqueous solution comprises at least about 1.0 g/L carbon source. According to an embodiment, said first aqueous solution comprises less than about 500 g/L carbon source.

According to an embodiment, said carboxylic acid is selected from a group consisting of acetic acid, butyric acid, lactic acid and mixtures thereof. According to an embodiment, said first aqueous solution comprises at least about 0.1 g/L carboxylic acid. According to an embodiment, said first aqueous solution comprises less than about 50 g/L carboxylic acid. According to an embodiment, said fermentation medium comprises at least about 0.1 g/L carboxylic acid. According to an embodiment, said fermentation medium comprises less than about 50 g/L carboxylic acid.

According to an embodiment, said first aqueous solution comprises at least about 0.1 wt %, e.g., at least about 0.2 wt %, 0.3 wt %, 0.5 wt %, 0.6 wt %, 0.7 wt %, 0.8 wt %, 0.9 wt %, 1.0 wt %, 1.5 wt %, 2.0 wt %, or more, of said extractant. According to an embodiment, said first aqueous solution comprises less than about 100 g/L (e.g., at least 100 wt %) extractant. According to an embodiment, said fermentation medium comprises at least about 0.1 wt %, e.g., at least about 0.2 wt %, 0.3 wt %, 0.5 wt %, 0.6 wt %, 0.7 wt %, 0.8 wt %, 0.9 wt %, 1.0 wt %, 1.5 wt %, 2.0 wt %, or more, of said extractant. According to an embodiment, said fermentation medium containing recycled raffinate comprises less than about 100 g/L (e.g., at least 100 wt %) extractant.

According to an embodiment, said first aqueous solution comprises at least one fermentation coproduct additional to carboxylic acid. According to a related embodiment, said fermentation coproduct is at least one of ethanol and acetone.

According to an embodiment, said first aqueous solution comprises at least about 0.1 g/L ethanol. According to an embodiment, said first aqueous solution comprises less than about 100 g/L ethanol. According to an embodiment, said fermentation medium comprises at least about 0.1 g/L ethanol. According to an embodiment, said fermentation medium comprises less than about 100 g/L ethanol.

According to an embodiment, said first aqueous solution does not comprise acetone. According to an embodiment, said first aqueous solution comprises greater than 0.1 g/L acetone. According to an embodiment, said first aqueous solution comprises less than 100 g/L acetone. According to an embodiment, said fermentation medium does not comprise acetone. According to an embodiment, said fermentation medium comprises at least greater than 0.1 g/L acetone. According to an embodiment, said fermentation medium comprises less than 100 g/L acetone.

According to an embodiment, ethanol and acetone concentrations in at least one of the raffinate and the fermentation medium is determined by extractant choice and by extractant to broth ratio in said contacting, as explained in the following.

The method of the first aspect comprises repeating the steps of forming the fermentation medium and of fermenting the formed medium. According to the method, said first aqueous solution comprises the raffinate from contacting (extracting) the broth of the earlier cycle fermentation. According to an embodiment, said extraction raffinate is used as said first aqueous solution or is modified to form said first aqueous solution. According to related embodiments, modifying said raffinate comprises at least one of vaporizing extractant comprised in it, temperature change, addition or removal of water, addition of another component and heat treatment.

The separated raffinate comprises extractant. While still under pressure, the raffinate comprises extractant at a concentration of at least 150 g/L. On application of heat and, optionally, pressure reduction, the majority of the extractant is vaporized and the resultant extraction concentration reduced to between 1 and 80 g/L. Residual extractant concentration in the depressurized raffinate depends on its pressure and temperature. Surprisingly, the recycled raffinate, containing residual extractant, does not result in growth inhibition or solventogensis inhibition. Further surprisingly, the residual extractant level appears to inhibit the growth of competing organisms. Because of these surprising results, the raffinate does not need to be sterilized before being recycled into a subsequent fermentation medium or fermentation broth.

i. Fermentation

The method of the first aspect comprises fermenting said medium with a butanol producing organism to form a broth comprising butanol, said carboxylic acid, a carbon source, a nitrogen source and extractant. According to an embodiment, said fermentation medium is inoculated with said organism.

According to an embodiment, a fraction of the carbon source in the fermentation medium and optionally also part of the nitrogen source is consumed during said fermentation, resulting in the formation of butanol and optionally also coproducts, such as ethanol, acetone or both. According to another embodiment, at least a fraction of the carboxylic acid in the fermentation medium is also assimilated. According to an embodiment, said fermentation is conducted in a fermentor. According to a related embodiment, a fraction of the extractant in the fermentation medium is removed from the fermentor along with other vapors, e.g. $CO_2$.

According to an embodiment, said organism is characterized by resistance to (e.g., ability or capability to be viable in) extractant at a concentration of at least about 1.0 g/L, e.g., at least about 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, or 95 g/L, and up to about 100 g/L.

According to an embodiment, said organism is resistant to extractant concentration greater than 1.0 g/L to butanol concentration greater than 1.0 g/L, to ethanol concentration greater than 1.0 g/L, to acetone concentration greater than 1.0 g/L, and to combinations thereof.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of butanol production, e.g., including without limitation *Firmicutes*, e.g., including without limitation *Clostridia*. Illustrative *Clostridia* include, e.g., *Clostridium* and *Eubacterium*. Illustrative *Clostridium* of these include without limitation, *Clostridium butyricum*, *Clostridium acetobutylicum*, *Clostridium saccharoperbutylacetonicum*, *Clostridium saccharobutylicum*, *Clostridium beijerickii*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum*, *Clostridium autoethanogenum*. Illustrative *Eubacterium* include *Eubacterium limosum*.

Suitable bacteria and fungi also include those that are capable of hydrolyzing carbon sources and can be genetically engineered to produce butanol. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus, Saccharomycopsis, Aspergillus, Pichia, Schwanniomyces* and *Polysporus*. The fungi may be able to do the conversion aerobically or anaerobically. Examples of anaerobic fungi include, without limitation, *Piromyces* species (e.g., strain E2), *Orpinomyces* species (e.g. *Orpinomyces bovis*), *Neocallimastix* species (*N. frontalis*), *Caecomyce* species, *Anaeromyces* species and *Ruminomyces* species.

As noted above, any microorganism, whether naturally occurring or manmade, that is capable of producing butanol can be used and the methods described herein are not limited to the examples listed here. In some embodiments, the microorganism is viable at temperatures from about 20° C. to about 95° C. Reference to a microorganism being viable at a given temperature or range of temperatures refers to a microorganism being able to survive exposure to such temperatures and subsequently be able to grow and/or produce metabolic products under the same or different conditions. In other embodiments, the microorganism is a temperature resistant microorganism. In other embodiments, the microorganism is an extractant resistant microorganism. The term "resistance" is defined as the property of a biocatalyst to have a low rate of growth inhibition and solventogenis inhibition in the presence of increasing concentrations of an inhibitor in the fermentation broth.

In some embodiments, the microorganism has a productivity of at least about 0.5 g/L per hour of butanol in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour of the C2 and C4 alcohol in aggregate over the lifetime of a batch fermentation cycle. In some embodiments, the productivity ranges from about 0.5 g/L per hour to about 5 g/L per hour of the butanol over the lifetime of a batch fermentation cycle.

According to an embodiment, said broth comprises at least about 0.1 g/L, e.g, at least about 1.0 g/L, 10 g/L, 20 g/L, 30 g/L, 40 g/L, 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, or 190 g/L butanol. According to an embodiment, said broth comprises less than about 200 g/L butanol (e.g., in the range of about 0.1 g/L to about 200 g/L).

According to an embodiment, said broth comprises at least about 1 g/L carbon source. According to an embodiment, said broth comprises less than about 400 g/L carbon source.

According to an embodiment, said broth comprises at least about 0.1 g/L carboxylic acid. According to an embodiment, said broth comprises less than about 100 g/L carboxylic acid.

Fermentation produces gaseous coproducts that, in turn, gas strips out extractant that was recycled through the raffinate. Accordingly, in one embodiment, said broth comprises reduced amounts of extractant. According to an embodiment, said broth comprises at least about 0.1 g/L extractant. According to an embodiment, said broth comprises less than about 10 g/L extractant, e.g., less than about 9 g/L, 8 g/L, 7 g/L, 6 g/L, 5 g/L, 4 g/L, 3 g/L, 2 g/L, 1 g/L, 0.5 g/L, 0.4 g/L, 0.3 g/L, 0.2 g/L, or less, extractant.

According to an embodiment, said broth comprises at least about 0.1 g/L ethanol. According to an embodiment, said broth comprises less than about 100 g/L ethanol.

According to an embodiment, said broth does not comprise acetone. According to an embodiment, said broth comprises greater than about 0.01 g/L acetone. According to an embodiment, said broth comprises less than about 100 g/L acetone.

According to an embodiment, wherein said carbon source comprises liquefied corn, the method of the first aspect comprises separating wet solids from said broth prior to said contacting. Any form of solids separation is suitable. According to an embodiment, said separation uses at least one of centrifugation and filtration.

ii. Extraction

The method of the first aspect comprises contacting said broth with an extractant to form an extract and a raffinate, wherein said extract comprises said extractant, butanol and water and wherein said raffinate comprises said carboxylic acid, a carbon source, a nitrogen source and extractant. Said contacting is also referred to in the following as extracting. In a following step, said extract is separated from said raffinate.

According to an embodiment, during contacting with the extractant, the broth is maintained at a pH greater than about 6, e.g. in the range between about 6 and about 10, e.g., between about 6 and about 9, or between about 6.1 and about 8 or between about 7 and about 9, e.g., between about 8 and about 9. According to an embodiment, the method of the first embodiment comprises checking the pH of said broth and if under 6, contacting with a base to adjust it to above 6. According to an embodiment, said contacting with a base comprises adding a base to the broth, e.g. adding sodium hydroxide (NaOH) or potassium hydroxide (KOH). Alternatively or additionally, said contacting comprises contacting with a basic ion-exchanger, e.g. one carrying an amine function or carrying a weak acid function in a salt form.

The extractant boiling point at atmospheric pressure under 20° C. Its Hansen solubility parameter polarity component is in the range between 2 $MPa^{0.5}$ and 8 $MPa^{0.5}$ and its Hansen solubility parameter H-bond component is in the range between 2 $MPa^{0.5}$ and 8 $MPa^{0.5}$.

According to an embodiment said extractant comprises an ether selected from the group consisting of dimethyl ether (DME), methyl ethyl ether (methoxyethane), and mixtures thereof. According to an embodiment said extractant is selected from the group consisting of dimethyl ether (DME), methyl ethyl ether, and mixtures thereof. According to an embodiment, at least about 95%, at least about 98% or at least about 99% of the extractant is selected from the group consisting of dimethyl ether (DME), methyl ethyl ether (methoxyethane), and mixtures thereof.

In various embodiments, said contacting is conducted at a temperature in the range of about 20° C. to about 35° C., for example, about 20° C., 21° C., 22° C., 23° C., 24° C., 25° C., 26° C., 27° C., 28° C., 29° C., 30° C., 31° C., 32° C., 33° C., 34° C. or 35° C. In various embodiments, contacting is conducted at a fermentation temperature. For example, for certain organisms, fermentation temperature is in the range of about 35° C. to about 40° C., for example at a temperature of about 35° C., 36° C., 37° C., 38° C., 39° C. or 40° C.

In various embodiments, said contacting is conducted at above about 20 psi (1.38 bar; 1.36 atm) and below about 145 psi (10 bar; 9.87 atm), for example, about 20 psi (1.38 bar; 1.36 atm; 87 psi (6 bar; 5.9 atm); 102 psi (7 bar; 6.9 atm); 116 psi (8 bar; 7.9 atm); 131 psi (9 bar; 8.9 atm); or 145 psi (10 bar; 9.87 atm).

Any form of contacting is suitable. Any form of extract separation from the raffinate is suitable. According to an embodiment, said contacting comprises multiple-stage contacting, e.g., having between 2 and 40 stages, e.g., between 2 and 30, 2 and 20, 2 and 10 or 2 and 6 stages. According to an embodiment, contacting is conducted in a countercurrent mode. According to various embodiments, contacting and separation are conducted in a column operation or in a set of mixer settlers.

For example, gas-phase DME can be bubbled up through a vertical column through which the aqueous solution is being poured down.

According to an embodiment, extraction uses a column contactor. The column can be adjusted in length and width (e.g., internal diameter) to enable sufficient residence time contact between the aqueous solution with the rising DME in the column. In varying embodiments, the columns can be as short as 10 cm and as long as 30 m, for example, about 0.01 m, 0.05 m, 0.10 m, 0.5 m, 1.0 m, 1.5 m, 2.0 m, 2.5 m, 3.0 m, 3.5 m, 4.0 m, 4.5 m 5.0 m, 5.5 m, 6.0 m, 6.5 m, 7.0 m, 7.5 m, 8.0 m, 8.5 m, 9.0 m, 9.5 m, 10 m, 15 m, 20 m, 25 m or 30 m. In some embodiments, the column has a length in the range between 2 m and 5 m.

In varying embodiments, the column inside diameter (ID) can be in the range of about 0.01 m to about 10 m, e.g., about 0.01 m, 0.04 m, 0.05 m, 0.08 m, 0.10 m, 0.5 m, 1 m, 1.5 m, 2 m, 2.5 m, 3 m, 3.5 m, 4 m, 4.5 m, 5 m, 6 m, 7 m, 8 m, 9 m or 10 m. In some embodiments, the ID is in the range of between about 0.04 m and about 2.0 m. In varying embodiments, the length/ID ratio is in the range of between about 5 and about 200, e.g., about 5, 10, 20, 25, 50, 75, 100, 125, 150, 175 or 200. In some embodiments, the length/ID ratio is in the range of between about 20 and about 60, e.g., about 20, 25, 30, 35, 40, 45, 50, 55 or 60.

In varying embodiments, the superficial flow velocity as defined by the ratio of the total volumetric flow to the inside column area is in the range of between about 0.1 cm/sec and about 100 cm/sec, e.g., 0.1 cm/sec, 0.5 cm/sec, 1.0 cm/sec, 5 cm/sec, 10 cm/sec, 15 cm/sec, 20 cm/sec, 25 cm/sec, 50 cm/sec, 75 cm/sec, or 100 cm/sec. In some embodiments, the superficial flow velocity as defined by the ratio of the total volumetric flow to the inside column area is in the range of between about 5 to about 15 cm/sec.

According to varying embodiments, the flux ratio of extractant to broth is in the range of from about 0.5 to about 20, e.g., about 0.5, 1, 2, 3, 4, 5, 6, 7, 8, 9, 10, 11, 12, 13, 14, 15, 16, 17, 18, 19, or 20. In some embodiments, the flux ratio of extractant to aqueous solution is in the range of from about 1 to about 3.

Methods for performing liquid-liquid extraction ("LLE") in a countercurrent column have been well documented in the literature, e.g., by Treybal, Robert E., "Liquid Extraction," McGraw-Hill, New York, 1951). Each countercurrent stage can be implemented with a mixer and settler. As an integrated system with multiple stages, a spray tower may be used (e.g., per FIG. 10.1 in Treybal). In addition, conventional tray columns using disk and donut baffles find use (FIGS. 10.4a and 10.4b in Treybal). Further, a column with random packing and flow distributor regions, using packing such as raschig rings, Pall Rings, Intalox saddles, or berl saddles, find use. In addition, a Podbielniak extractor could optionally be used (FIG. 10.12 in Treybal). Such devices are also described, e.g., in Perry's Chemical Engineering Handbook (Chapter 15, 8th edition, 2008). Columns that find use in the present extraction methods include static extraction columns, agitated extraction columns, mixer-settlers, or centrifugal extractors. Any one of these configurations can be configured to implement the desired number of stages. Economics, as constrained by throughput and equipment space constraints, would define the preferred configuration. An illustrative multistage centrifugal extractor is available from Robatel, Inc. (on the internet at rousselet-robatel.com/products/multistage-centrif-extractors-lx.php). Use of centrifugal countercurrent columns for continuous LLE is also described, e.g., on the internet at cheresources.com/centcontactor.shtml.

iii. Extraction Yields and Selectivity and Buildup of Ethanol and Acetone

Said extractant has limited solubility in the aqueous broth, so that above a given phase ratio, two phases are formed. Contacting according to the method of the first aspect is conducted at a ratio wherein two phases are formed and butanol transfers into the extractant-rich phase. Such transfer into that phase is also referred to herein as extraction-butanol is extracted into the extractant-rich phase. As a result, the formed extract comprises at least a fraction of the butanol originally present in the broth and the formed raffinate is depleted in butanol. The extent of butanol transfer to the extract (also referred to as extraction yield) is determined by several parameters, including: extractant properties, as indicated by the distribution coefficient, extractant to broth counter-current flux ratio, the number of contact stages and the residence time in each stage. For a given extractant, a given number of stages and typical contacting operation, the extraction yield is determined by the flux ratio. Extraction yield increases with said ratio.

According to the method of the first aspect, extractant to broth ratio (more specifically flux ratio in case of countercurrent mode) in said contacting is selected so that the formed extract comprises at least about 40%, e.g., at least about 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, of the butanol in the broth. According to an embodiment, butanol concentration in the broth is in the range between about 1 g/L and about 100 g/L, the flux ratio is in the range between about 0.5 and about 20 and extraction yield is greater than about 40%, e.g., greater than about 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more.

Additionally to butanol, water also transfers into the extractant—is co-extracted—so that the extract comprises both butanol and water. The distribution coefficient of water, in case of the used extractant, is smaller than that of butanol, i.e. the extractant is selective to butanol over water. According to an embodiment, due to that selectivity, the butanol/water ratio in the extract is greater than that in the broth and greater than that in the raffinate (although typically no equilibrium is reached in an industrial operation and although contacting is of multiple stages). According to an embodiment, butanol/water ratio in the extract is greater than 0.1, e.g., 0.2, 0.3, 0.4, 0.5, 0.6, 0.7, 0.8, 0.9, 1.0, or greater.

According to an embodiment, additionally to butanol and water, other broth components are extracted. According to an embodiment, using said extractant, butanol is extracted selectively over such other components, i.e. its distribution coefficient is greater than theirs. As in the case of butanol extraction, the extent of extraction of such other components is determined by the extractant/broth flux ratio. Typically, due to the smaller distribution coefficient, high yields of extraction of such other components require greater extractant/broth flux ratio. According to an embodiment of the first aspect, the selected flux ratio is sufficient for high butanol extraction yield, but smaller than required for such high yield of extracting components other than butanol. As a result, the fraction of the broth butanol in said extract (butanol extraction yield) is greater than the fraction of the broth other component in said extract (extraction yield of the other component).

According to an embodiment, said broth comprises ethanol and extractant to broth ratio in said contacting is selected so that the fraction of the broth butanol in said extract is greater than the fraction of the broth ethanol in said extract. According to an embodiment, butanol extraction yield is greater than ethanol extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to an embodiment, at least about 10%, e.g., at least about 20%, 30%, 40%, 50%, 60%, 70%, 80%, or more, of the ethanol, originally present in the broth, remains in the raffinate.

According to an embodiment, said broth comprises acetone and extractant to broth ratio in said contacting is selected so that the fraction of the broth butanol in said extract is greater than the fraction of the broth acetone in said extract. According to an embodiment, butanol extraction yield is greater than acetone extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to an embodiment, at least about 10%, e.g., at least about 20%, 30%, 40%, 50%, 60%, 70%, 80%, or more, of the acetone, originally present in the broth, remains in the raffinate.

According to an embodiment, said extract comprises less than about 10%, e.g., less than about 9%, 8%, 7%, 6%, 5%, 4%, 3%, 2%, 1% or 0.5%, of the carboxylic acid in said broth, i.e. carboxylic acid extraction yield is less than about 10%, e.g., less than about 9%, 8%, 7%, 6%, 5%, 4%, 3%, 2%, 1% or 0.5%. Additionally or alternatively, the carbon source extraction yield is less than about 10%, e.g., less than about 9%, 8%, 7%, 6%, 5%, 4%, 3%, 2%, 1% or 0.5%. Additionally or alternatively, the nitrogen source extraction yield is less than about 10%, e.g., less than about 9%, 8%, 7%, 6%, 5%, 4%, 3%, 2%, 1% or 0.5%. Additionally or alternatively, the extraction yield of other nutrient, e.g. vitamins and minerals, is less than about 10%, e.g., less than about 9%, 8%, 7%, 6%, 5%, 4%, 3%, 2%, 1% or 0.5%.

According to these and similar embodiments, the raffinate contains only a small fraction of the broth original butanol content, e.g. less than about 15%, e.g., less than about 10%, 5%, or less, of the original butanol content, but large fractions of the other broth components, e.g. more than about 30%, e.g., more than about 40%, 50%, 60%, 70%, 80%, or more, of the ethanol, more than about 30%, e.g., more than about 40%, 50%, 60%, 70%, 80%, or more, of the acetone, more than about 50%, e.g., more than about 60%, 70%, 80%, or more, of the carboxylic acid, more than 50%, e.g., more than about 60%, 70%, 80%, or more, of the carbon source, more than about 50%, e.g., more than about 60%, 70%, 80%, or more, of the nitrogen source, more than about 50% of other nutrients and combinations thereof.

The method of the first aspect comprises repeating the steps of forming the fermentation medium and of fermenting the formed medium. According to the method, said first aqueous solution comprises the raffinate from contacting (extracting) the broth of the earlier cycle fermentation. According to an embodiment, said formed first aqueous solution comprises most or all the broth components contained in the raffinate of the earlier cycle. According to an embodiment, said formed fermentation medium comprises most or all the broth components contained in the raffinate of the earlier cycle. According to an embodiment, said carbon source, nitrogen source, other nutrient and carboxylic acid in said fermentation medium serve the production of additional amount of butanol, saving thereby on costs of carbon sources and nutrients.

According to an embodiment, said fermentation medium comprises ethanol originally in the broth of the earlier cycle and said microorganism does not consume it or consumes only a small fraction of it. According to an embodiment, additional ethanol is generated during the fermentation. According to an embodiment, the ethanol concentration in the formed broth is greater than in the case where raffinate of the previous cycle is not used to form the fermentation medium. Additionally or alternatively, according to an embodiment, said fermentation medium comprises acetone originally in the broth of the earlier cycle and said microorganism does not consume it or consumes only a small fraction of it. According to an embodiment, additional acetone is generated during the fermentation. According to an embodiment, the acetone concentration in the formed broth is greater than in the case where raffinate of the previous cycle is not used to form the fermentation medium. In varying embodiments, the fermentation medium does not comprise acetone.

Hence, according to various embodiments, the concentration of ethanol, acetone or both in the formed broth is greater than in the case where raffinate of the previous cycle is not used to form the fermentation medium. Additionally, the broth contains some extractant. It was found that the organism is resistant to said relatively high levels of extractant and ethanol and/or acetone in both the growth phase and stationary phase.

Hence, according to various embodiments, the method is characterized by selecting an extractant and extractant/broth ratio that lead to high butanol extraction yields, but low yields on extraction of other components so that these other components remain in the raffinate; by using said raffinate to form the fermentation medium of the next cycle, by the relatively high concentration of fermentation coproduct (carboxylic acid, ethanol and/or acetone) in said fermentation medium; by resulting extractant concentration in the fermentation medium and by efficient fermentation in the medium comprising said coproducts and extractant.

iv. Extractant Separation from the Extract and Recycle to Extraction

The method of the first aspect comprises separating extractant from at least a fraction of said extract to form separated extractant and extractant-depleted extract and separating butanol from at least a fraction of said extractant-depleted extract to form a first butanol stream.

According to an embodiment, said extractant separation from the extract comprises application of heat and, optionally, pressure reduction, whereby extractant evaporates. Hence, according to an embodiment, both contacting the extractant and extract separation from the raffinate are conducted at super-atmospheric pressure, followed by reducing the pressure of the extract whereby the extractant evaporates. According to an embodiment, the vaporized extractant is separated and then condensed to reform the extractant for contacting in the following cycle. According to an embodiment, said vaporizing and said condensing are driven by a refrigerant circuit.

The energetics of using, reusing and recycling extractant, e.g. DME, are improved by driving its vaporization and condensation using a heat pump or refrigerant circuit. In one embodiment, the refrigerant used allows the temperature range for the extractant to fluctuate from about 20° C. to about 30° C., where 20° C. is the condensation temperature and 30° C. is the flash-to-vaporization temperature. To drive this temperature difference, a heat pump with conditions that go between 15° C. and 35° C. is used. Thus, there is a 5° C. temperature difference to drive both condensation and vaporization. In this temperature range, the refrigerant R-134a finds use. At 15° C., R-134a condenses 20° C. DME and at 35° C., R134a vaporizes 30° C. DME. In this particular case, the amount of energy to drive the DME loop is calculated to be 0.0095 kW/(kg/hr) or 9.5 kW/1000 kg/hr DME flow based on thermal balance and thermodynamic properties of the DME and R-134a.

Other temperature ranges/pressures will work, and other refrigerants, also find use. In some embodiments, the refrigerant used to drive the heat pump or refrigerant circuit is selected from R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R 236ea, R 245ca, R-365mfc, RC318, R 406a, R-410a, R-414a, R-500, R-502, R-503, R-1301 and ammonia.

In other embodiments, the extractant is condensed using vapor recompression. Vapor recompression is simpler and is commonly used in the oil and gas industries. However, implementing vapor recompression requires a compressor of specific design for use with flammable extractant (e.g. DME). Use of a refrigerant circuit has the advantage that it can be implemented with commercial off-the-shelf refrigerant equipment (e.g., refrigerant compressors, expansion valves, heat exchangers).

v. Formation of Butanol-Rich Organic Solution and Second Aqueous Solution and Recovery of Butanol from these Streams According to an embodiment, said separating butanol from at least a fraction of said extractant-depleted extract comprises distillation.

Since the organism exhibits resistance to relatively high concentrations of ethanol and acetone in the presence of the extractant, the organism is reaching relatively high butanol concentration in the fermentation broth. Said relatively high concentration combined with the selectivity of the extractant to butanol over water, result in relatively high butanol/water ratio in the extract. According to an embodiment, said ratio is greater than 0.2, e.g., greater than 0.3, 0.4, 0.5, 0.6, 0.7, 0.8, 1.0, 1.1, 1.2, 1.3, 1.4, 1.5, 1.6, 1.7, 1.8, 1.9, 2.0, or greater. According to an embodiment, said ratio is such that on an extractant-free basis butanol concentration is greater than butanol solubility in water.

According to an embodiment, said butanol/water ratio is such that said extractant-depleted extract, as such or after combining with other butanol-comprising streams, comprises (or is split into) two phases: a butanol-rich organic solution and a butanol comprising second aqueous solution. Said split into two phases indicates butanol concentration greater than saturation in the extractant-depleted extract. In the butanol-water binary system, butanol solubility at atmospheric pressure and about 25° C. depends on the nature of the butanol—about 7%, 8% and 22% for n-butanol, isobutanol and sec-butanol, respectively. Yet, according to an embodiment, the extract also comprises ethanol, acetone or both. These coproducts act as co-solvents improving the mutual solubility of butanol and water. Hence, the split of the extractant-depleted extract into two phases is a result of adjusting a combination of the method parameters: butanol concentration in the broth (depending on carbon source concentration in the fermentation medium, on organism selection as well as on other parameters); butanol concentration in the extract (extractant choice and implications for the butanol distribution coefficient, flux ratio, and more); butanol/water selectivity (extractant choice, broth composition affecting water activity); ethanol and acetone concentration in the extract (organism choice, extractant choice and flux ratio, butanol concentration, etc.) and means for extractant separation from the extract. According to an embodiment, these parameters are further adjusted in order to maximize the ratio between the butanol-rich organic solution and the butanol comprising second aqueous solution.

The split of the extractant-depleted extract forms a butanol-rich organic solution comprising, according to an embodiment, at least about 30%, e.g., at least about 35%, 40%, 45%, 50%, 55%, 60%, 65%, 70%, 75%, 80%, 85%, 90%, 95%, 96%, 97%, 98%, 99%, 99.5%, or greater, butanol. According to an embodiment, this butanol-rich organic solution is separated from said second aqueous solution, by known means, such as decanting in a suitable decanter. According to an embodiment, the separated organic solution is distilled to form refined butanol. The high butanol concentration in that organic solution saves on energy costs for generating said refined butanol.

According to an embodiment, said broth comprises a coproduct selected from ethanol, acetone or both, said extract comprises a fraction of said broth coproduct and said separated butanol-rich organic solution comprises at least a fraction of the coproduct in the extract. According to an embodiment, said coproduct is ethanol and distilling said separated butanol-rich organic solution forms refined butanol and separated ethanol. According to an embodiment, said coproduct is acetone and distilling said separated butanol-rich organic solution forms refined butanol and separated acetone. According to an embodiment, said coproduct comprises both ethanol and acetone and distilling said separated butanol-rich organic solution forms refined butanol, separated ethanol and separated acetone. According to an embodiment, the broth further comprises a product comprising one or more products from the list of n-butanol, isobutanol, or sec-butanol and coproducts comprising ethanol and one or more carboxylic acids.

According to an embodiment, butanol concentration in said butanol comprising second aqueous solution is in the range between about 30 g/L and about 250 g/L. According to an embodiment, said butanol comprising second aqueous solution still comprises a significant fraction of the broth butanol, e.g. more than about 5%, e.g., more than about 6%, 7%, 8%, 9%, 10%, 11%, 12%, 13%, 14%, 15%, or more, and said method of the first aspect comprises separating butanol from at least a fraction of said second aqueous solution to form a first butanol stream and a butanol-depleted residue. According to an embodiment, butanol is separated from at least two different fractions of said second aqueous solution and said separation differs between the fractions. According to an embodiment, at least one of those fractions is combined with another process stream before said butanol separation.

According to an embodiment, wherein said carbon source comprises liquefied corn and solids are separated from the broth prior to said contacting with the extractant and wherein said extractant-depleted extract comprises a butanol-rich organic solution and a butanol comprising second aqueous solution, the method of the first aspect comprises contacting said separated wet solids with a fraction of said second aqueous solution to form a mixture and separating butanol from said mixture to form a first butanol stream and a butanol-depleted residue. According to an embodiment, separating butanol from said mixture (typically a slurry of the solids in said second aqueous solution) comprises distillation forming a butanol-comprising vapor phase (the first butanol stream) and a butanol-depleted solid or suspension (the butanol-depleted residue).

According to an embodiment, said second aqueous solution comprises at least one of ethanol and acetone and said first butanol stream also comprises at least one of ethanol and acetone. According to an embodiment, said first butanol stream is combined with at least one other butanol-comprising stream to form a combined stream for further processing. According to an embodiment, said first butanol stream is combined with the extract, with a stream formed in distilling said butanol-rich organic solution or both. According to an embodiment, said combined stream is split into said butanol-rich organic solution and said second aqueous solution.

According to an embodiment, said solids-comprising butanol-depleted residue is used as an ingredient in animal feed. According to an embodiment, the first aspect of the invention provides an animal feed composition comprising at least a fraction of said butanol-depleted residue. According to an embodiment, the first aspect of the invention further provides a method for the production of said animal feed composition, comprising at least one of treating said butanol-depleted residue with an enzyme having phytase activity and drying.

According to an embodiment, butanol separation from at least a fraction of said second aqueous solution comprises at least one of distillation and extraction. According to an embodiment, said fraction of the second aqueous solution is combined with another process stream before said at least one of distillation and extraction. According to an embodiment, said fraction of the second aqueous solution is combined with the fermentation broth prior to said contacting with the extractant. Additionally or alternatively, said at least a fraction of said second aqueous solution is contacted with at least a fraction of said extract to form a butanol-depleted solution and a butanol enriched extract.

Hence, according to an embodiment, extraction is conducted in a column equipped with at least three input ports, first one at the bottom or near the bottom, a second one at the top or near the top and a third one between the two, e.g. at the upper half of the column. The column also has at least two output ports, a first one at the bottom or near the bottom and second one at the top or near the top and above the second input port. The extractant is fed to the column through the first input port, flows upwards and exits through the second output port. The fraction of the second aqueous solution is fed through the second input port and the broth through the third input port and the combined formed raffinate exits via the first output port. Alternatively, extraction is conducted through a battery of mixer-settlers with three input ports and two output ports, and similarly to the column case, the extractant and the second aqueous solution are introduced at the two ends and the broth is introduced along the way. Extraction according to these embodiments generates an extract with butanol/water ratio greater than that formed on extracting a mixture of the broth and the second aqueous solution.

vi. Repeat and Recycle

The method of the first aspect comprises the steps of combining a carbon source with a first aqueous solution to form a fermentation medium; fermenting said medium with a butanol producing organism to form a broth comprising butanol and optionally also at least one of ethanol and acetone; extracting said broth with an extractant to form an extract and a raffinate; separating said extract from said raffinate; separating extractant from at least a fraction of said extract to form separated extractant and extractant-depleted extract; separating butanol from at least a fraction of said extractant-depleted extract to form a first butanol stream; optionally using liquefied corn as the carbon source and separating wet solids from the broth prior to extraction; optionally splitting said extractant-depleted extract or its combination with other streams into a butanol-rich organic solution and butanol comprising second aqueous solution; optionally distilling said butanol-rich organic solution to form refined butanol and optionally an ethanol stream and an acetone stream; optionally contacting said separated wet solids with a fraction of said second aqueous solution to form a mixture and separating butanol from said mixture to form butanol-depleted residue and other optional steps; and repeating said steps.

Referring to the set of steps to be repeated as a cycle, streams formed in a given cycle are used in the following cycle, also referred to herein as recycled streams. Thus, the raffinate of a cycle is used to form the first aqueous solution and the fermentation medium of the next cycle. Differently put, the raffinate is recycled to form the fermentation medium. According to an embodiment, the raffinate is not further sterilized prior to being recycled into a subsequent fermentation medium. Similarly, the extractant separated from the extract of a cycle is used to form the extractant in the next cycle, i.e. is recycled to the extraction step.

According to various embodiments, recycled streams are treated or modified prior to reuse. For example, the extractant vaporized in separation from the extract is condensed prior to reuse in extraction, optionally using a refrigerant circuit. According to one embodiment, the extractant is removed from the raffinate prior to recycling in order to minimize extractant content there. According to another embodiment, a bleed is removed from the raffinate prior to recycling in order to avoid buildup of impurities.

vii. An Exemplary Method of the First Aspect

An embodiment of the first aspect is presented below with reference to FIG. 1. Recycled raffinate (112), comprising at least one carboxylic acid, a carbon source, a nitrogen source and extractant, is used as such or after modification to form a first aqueous solution (101). That first aqueous solution is combined in (103) with liquefied corn carbon source (102), whereby a fermentation medium (105) is formed. The fermentation medium is inoculated with butanol producing organism (104) for fermenting (106) which generates a broth (107) comprising butanol, ethanol, acetone, at least one carboxylic acid, a nitrogen source, extractant and solids. Wet solids (109) are separated in (108) to form low-solids broth (110). That broth and a fraction of a second aqueous solution (121) are extracted counter-currently in (111) with recycled extractant (118). The generated aqueous solution is treated for extractant vaporization in (133), whereby the raffinate to be recycled (112) is formed. The extract generated in the extraction (113) is treated in (114) for vaporizing extractant therefrom. The separated extractant vapors (116) are condensed in (117) to reform the extractant (118) for recycle to extraction. The extractant-depleted extract (115), combined with a first butanol stream (124) is decanted in (119) to form a butanol-rich organic solution (120) comprising also ethanol and acetone and a second aqueous solution comprising butanol, ethanol and acetone. Said butanol-rich organic solution is distilled in (129) to form refined butanol (132), separated ethanol (131) and separated acetone (130). A fraction of the second aqueous solution (121) is directed to extraction in (111). Another fraction (122) is contacted with the wet solids (109) in (136) to form a mixture (137). That mixture is distilled in (123) to form the first butanol stream (124) and a butanol-depleted residue (125). Said residue is treated (127) with an enzyme having phytase activity (126) and optionally dried to form an animal feed composition (128).

b. Method of the Second Aspect

According to a second aspect, provided is a method for producing butanol comprising (i) fermenting a fermentation medium with a butanol producing organism to form a broth comprising butanol, a coproduct selected from a group consisting of ethanol, acetone and combinations thereof, and at least one carboxylic acid; (ii) checking the pH of said broth and if under 6, contacting with a base to adjust it to above 6; (iii) contacting said broth with an extractant to form an extract and a raffinate, wherein said extract comprises said extractant, butanol, water and said coproduct and wherein said raffinate comprises said carboxylic acid; (iv) separating said extract from said raffinate; (v) separating extractant from at least a fraction of said extract to form separated extractant, a butanol-rich organic solution comprising said coproduct, and butanol comprising second aqueous solution; and (vi) distilling said butanol-rich organic solution to form refined butanol and separated coproduct; wherein; (a) extractant boiling point at atmospheric pressure is under 20° C.; (b) extractant Hansen solubility parameter polarity component is in the range between 2 $MPa^{0.5}$ and 8 $MPa^{0.5}$; (c) extractant Hansen solubility parameter H-bond component is in the range between 2 $MPa^{0.5}$ and 8 $MPa^{0.5}$; and (d) extractant to broth ratio in said contacting is selected so that the formed extract comprises at least about 35%, e.g., at least about 40%, 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, of the butanol in the broth.

According to an embodiment, the fermentation medium of the second aspect comprises at least one carbon source, a nitrogen source and nutrients. According to various embodiments, it also comprises at least one carboxylic acid, extractant, ethanol, acetone or combinations thereof. According to an embodiment, recycled raffinate is used to form said fermentation medium. According to an embodiment, the raffinate is not further sterilized before being recycled to form the fermentation medium. According to an embodiment, a carbon source is used to form said fermentation medium. According to an embodiment, a carbon source is combined with recycled raffinate (as such or after modification) to form said fermentation medium. According to an embodiment, said carbon source is liquefied corn.

The method of the second aspect comprises fermenting said medium with a butanol producing organism to form a broth comprising butanol, said coproduct, at least one carboxylic acid and optionally also a carbon source, a nitrogen source, extractant and combinations thereof. According to an embodiment, said fermentation medium is inoculated with said organism.

In varying embodiments, the method of the second aspect comprises fermenting said medium with a *Clostridia* to form a broth comprising butanol and further comprising coproducts of one or more C3-C9 alcohols, one or more C3-C9 carboxylic acids, and optionally also a carbon source, a nitrogen source, extractant and combinations thereof. According to an embodiment, said fermentation medium is inoculated with said *Clostridia*.

According to an embodiment, said organism is characterized by resistance to (e.g., ability or capability to be viable in) extractant at a concentration of at least about 1.0 g/L, e.g., at least about 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, or 95 g/L, and up to about 100 g/L.

According to an embodiment, said organism is resistant to extractant concentration greater than 1.0 g/L, to butanol concentration greater than 1.0 g/L, to ethanol concentration greater than 1.0 g/L, to acetone concentration greater than 1.0 g/L, and to combinations thereof.

Suitable organisms are as described above (e.g. in embodiments for the method of the first aspect) and herein. According to an embodiment, suitable bacteria can include those that are capable of butanol production, e.g., including without limitation *Firmicutes*, e.g., including without limitation *Clostridia*. Illustrative *Clostridia* include, e.g., *Clostridium* and *Eubacterium*. Illustrative *Clostridium* of these include without limitation, *Clostridium butyricum*, *Clostridium acetobutylicum*, *Clostridium saccharoperbutylacetonicum*, *Clostridium saccharobutylicum*, *Clostridium beijerickii*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum*, *Clostridium autoethanogenum*. Illustrative *Eubacterium* include *Eubacterium limosum*.

According to an embodiment, said carboxylic acid is selected from a group consisting of acetic acid, butyric acid and lactic acid.

According to the method of the second aspect, during contacting with the extractant, the broth is maintained at a pH greater than about 6, e.g. in the range between about 6 and about 10, e.g., between about 6 and about 9, or between about 6.1 and about 8 or between about 7 and about 9, e.g., between about 8 and about 9. According to the method of the second aspect, the method comprises checking the pH of said broth and if under 6, contacting with a base to adjust it to above 6. According to an embodiment, said contacting with a base comprises adding a base to the broth, e.g., adding NaOH or KOH is a concentration of about 0.1 wt %, e.g., about 0.5 wt %, 1.0 wt %, 2.0 wt %, 5.0 wt %, 10 wt %, 20 wt %. Alternatively or additionally, said contacting comprises contacting with a basic ion-exchanger, e.g., one carrying an amine function or carrying a weak acid function in a salt form.

According to an embodiment, wherein said carbon source comprises liquefied corn, the method of the second aspect comprises separating wet solids from said broth prior to said contacting. Any form of solids separation is suitable.

According to an embodiment, said separation uses at least one of centrifugation and filtration.

The method of the second aspect comprises contacting said broth with an extractant to form an extract and a raffinate, wherein said extract comprises said extractant, butanol, water and said coproduct and wherein said raffinate comprises said carboxylic acid and optionally a carbon source, a nitrogen source, extractant and combinations thereof. Said contacting is also referred to in the following as extracting. In a following step, said extract is separated from said raffinate.

The extractant boiling point, at atmospheric pressure, is under 20° C. Its Hansen solubility parameter polarity component is in the range between 2 $MPa^{0.5}$ and 8 $MPa^{0.5}$ and its Hansen solubility parameter H-bond component is in the range between 2 $MPa^{0.5}$ and 8 $MPa^{0.5}$.

According to an embodiment said extractant comprises an ether selected from the group consisting of dimethyl ether (DME), methyl ethyl ether (methoxyethane), and mixtures thereof. According to an embodiment said extractant is selected from the group consisting of dimethyl ether (DME), methyl ethyl ether, and mixtures thereof. According to an embodiment, at least about 95%, at least about 98% or at least about 99% of the extractant is selected from the group consisting of dimethyl ether (DME), methyl ethyl ether (methoxyethane), and mixtures thereof.

In various embodiments, said contacting is conducted at a temperature in the range of about 20° C. to about 35° C., for example, about 20° C., 21° C., 22° C., 23° C., 24° C., 25° C., 26° C., 27° C., 28° C., 29° C., 30° C., 31° C., 32° C., 33° C., 34° C. or 35° C. In various embodiments, contacting is conducted at a fermentation temperature. For example, for certain organisms, fermentation temperature is in the range of about 35° C. to about 40° C., for example at a temperature of about 35° C., 36° C., 37° C., 38° C., 39° C. or 40° C.

In various embodiments, said contacting is conducted at above about 20 psi (1.38 bar; 1.36 atm) and below about 145 psi (10 bar; 9.87 atm), for example, about 20 psi (1.38 bar; 1.36 atm; 87 psi (6 bar; 5.9 atm); 102 psi (7 bar; 6.9 atm); 116 psi (8 bar; 7.9 atm); 131 psi (9 bar; 8.9 atm); or 145 psi (10 bar; 9.87 atm).

Any form of contacting is suitable. Any form of extract separation from the raffinate is suitable. According to an embodiment, said contacting comprises multiple-stage contacting, e.g., having between 2 and 40 stages, e.g., between 2 and 30, 2 and 20, 2 and 10 or 2 and 6 stages. According to an embodiment, contacting is conducted in a counter-current mode. According to various embodiments, contacting and separation are conducted in a column operation or in a set of mixer settlers.

According to varying embodiments, the flux ratio of extractant to broth is in the range of from about 0.5 to about 20, e.g., about 0.5, 1, 2, 3, 4, 5, 6, 7, 8, 9, 10, 11, 12, 13, 14, 15, 16, 17, 18, 19, or 20. In some embodiments, the flux ratio of extractant to aqueous solution is in the range of from about 1 to about 3.

According to a first embodiment of said second aspect, the extractant to broth flux ratio is selected so that at least about 70%, e.g., at least about 75%, 80%, 85%, 90%, 95%, 96%, 97%, 98%, 99%, 99.5%, or more, of both the butanol and said coproduct are extracted. According to said embodiment, said raffinate comprises less than about 30%, e.g., less than about 25%, 20%, 15%, 10%, or less, of both the butanol and said coproduct.

According to a second embodiment of the second aspect, the selected flux ratio is sufficient for high butanol extraction yield, but smaller than required for such high yield of extracting components other than butanol. As a result, the fraction of the broth butanol in said extract (butanol extraction yield) is greater than the fraction of the coproduct in said extract (extraction yield of the coproduct).

According to said second embodiment, said broth comprises ethanol and butanol extraction yield is greater than ethanol extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to an embodiment, said broth comprises acetone and butanol extraction yield is greater than acetone extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to said second embodiment, said extract comprises less than about 10%, e.g., less than about 9%, 8%, 7%, 6%, 5%, 4%, 3%, 2%, 1% or 0.5% of the carboxylic acid in said broth, i.e. carboxylic acid extraction yield is less than about 10%, e.g., less than about 9%, 8%, 7%, 6%, 5%, 4%, 3%, 2%, 1% or 0.5%. Additionally or alternatively, the carbon source extraction yield is less than about 10%, e.g., less than about 9%, 8%, 7%, 6%, 5%, 4%, 3%, 2%, 1% or 0.5%. Additionally or alternatively, the nitrogen source extraction yield is less than about 10%, e.g., less than about 9%, 8%, 7%, 6%, 5%, 4%, 3%, 2%, 1% or 0.5%. Additionally or alternatively, the extraction yield of other nutrient, e.g. vitamins and minerals, is less than about 10%, e.g., less than about 9%, 8%, 7%, 6%, 5%, 4%, 3%, 2%, 1% or 0.5%.

According to said second embodiment, the raffinate contains only a small fraction of the broth's original butanol content, e.g. less than about 15%, but large fractions of the other broth components, e.g. more than 30% of the ethanol, more than 30% of the acetone, more than 50% of the carboxylic acid, more than 50% of the carbon source, more than 50% of the nitrogen source, more than 50% of other nutrients and combinations thereof. According to said second embodiment, said raffinate, as such, or after pretreatment, is recycled to form said fermentation medium in a following cycle. In varying embodiments, the raffinate is not further sterilized prior to being recycled to form the fermentation medium.

The method of the second aspect comprises separating extractant from at least a fraction of said extract to form separated extractant, a butanol-rich organic solution comprising said coproduct, and butanol comprising second aqueous solution.

According to an embodiment, said extractant separation from the extract comprises application of heat and, optionally, pressure reduction, whereby extractant evaporates. Hence, according to an embodiment, both contacting the extractant and extract separation from the raffinate are conducted at super-atmospheric pressure, followed by application of heat and, optionally, reducing the pressure of the extract whereby the extractant evaporates. According to an embodiment, the vaporized extractant is separated and then condensed to reform the extractant for contacting in the following cycle. According to an embodiment, said vaporizing and said condensing are driven by a refrigerant circuit.

Said butanol-rich organic solution comprising, according to an embodiment, at least about 35%, e.g., at least about 40%, 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, butanol. According to an embodiment, this butanol-rich organic solution is separated from said second aqueous solution, by known means, such as decanting in a suitable decanter. According to the method of the second aspect said butanol-rich organic solution is distilled to form refined butanol and separated coproduct. The high butanol concentration in that organic solution saves on energy costs for generating said refined butanol.

According to an embodiment, said coproduct is ethanol and distilling said separated butanol-rich organic solution forms refined butanol and separated ethanol. According to an embodiment, said coproduct is acetone and distilling said separated butanol-rich organic solution forms refined butanol and separated acetone. According to an embodiment, said coproduct comprises both ethanol and acetone and distilling said separated butanol-rich organic solution forms refined butanol, separated ethanol and separated acetone.

According to an embodiment, butanol concentration in said butanol comprising second aqueous solution is in the range between about 10 g/L and about 250 g/L, e.g., at least about 10 g/L, 20 g/L, 30 g/L, 40 g/L or 50 g/L to about 150 g/L, 175 g/L, 200 g/L, 225 g/L, or 250 g/L. According to an embodiment, said butanol comprising second aqueous solution still comprises a significant fraction of the broth butanol, e.g. more than about 20%, e.g., more than about 25%, 30%, 35%, 40%, 45%, 50%, or more, of the broth butanol, and said embodiment comprises separating butanol from at least a fraction of said second aqueous solution to form a first butanol stream and a butanol-depleted residue. According to an embodiment, butanol is separated from at least two different fractions of said second aqueous solution and said separation differs between the fractions. According to an embodiment, at least one of those fractions is combined with another process stream before said butanol separation.

According to an embodiment, wherein said carbon source comprises liquefied corn and solids are separated from the broth prior to said contacting with the extractant, the method of the second aspect comprises contacting said separated wet solids with a fraction of said second aqueous solution to form a mixture and separating butanol from said mixture to form a first butanol stream and a butanol-depleted residue. According to an embodiment, separating butanol from said mixture (typically a slurry of the solids in said second aqueous solution) comprises distillation forming a butanol-comprising vapor phase (the first butanol stream) and a butanol-depleted solid or suspension (the butanol-depleted residue).

According to an embodiment, said second aqueous solution comprises said coproduct and said first butanol stream also comprises said coproduct. According to an embodiment, said first butanol stream is combined with at least one other butanol-comprising stream to form a combined stream for further processing. According to an embodiment, said first butanol stream is combined with the extract, with a stream formed in distilling said butanol-rich organic solution or both. According to an embodiment, said combined stream is split into said butanol-rich organic solution and said second aqueous solution.

According to an embodiment, said solids-comprising butanol-depleted residue is used as an ingredient in animal feed. According to an embodiment, the first aspect of the invention provides an animal feed composition comprising at least a fraction of said butanol-depleted residue. According to an embodiment, the second aspect of the invention further provides a method for the production of said animal feed composition, comprising at least one of treating said butanol-depleted residue with an enzyme having phytase activity and drying.

According to an embodiment, butanol separation from at least a fraction of said second aqueous solution comprises at least one of distillation and extraction. According to an embodiment, said fraction of the second aqueous solution is combined with another process stream before said at least one of distillation and extraction. According to an embodiment, said fraction of the second aqueous solution is combined with the fermentation broth prior to said contacting with the extractant. Additionally or alternatively, said at least a fraction of said second aqueous solution is contacted with at least a fraction of said extract to form a butanol-depleted solution and a butanol enriched extract.

Hence, according to an embodiment, extraction is conducted in a column equipped with at least three input ports, first one at the bottom or near the bottom, a second one at the top or near the top and a third one between the two, e.g. at the upper half of the column. The column also has at least two output ports, a first one at the bottom or near the bottom and second one at the top or near the top and above the second input port. The extractant is fed to the column through the first input port, flows upwards and exits through the second output port. The fraction of the second aqueous solution is fed through the second input port and the broth through the third input port and the combined formed raffinate exits via the first output port. Alternatively, extraction is conducted through a battery of mixer-settlers with three input ports and two output ports, and similarly to the column case, the extractant and the second aqueous solution are introduced at the two ends and the broth is introduced along the way. Extraction according to these embodiments generates an extract with butanol/water ratio greater than that formed on extracting a mixture of the broth and the second aqueous solution.

According to various embodiments, said fermentation medium comprises ethanol at a concentration greater than about 0.1 g/L, e.g., greater than about 1 g/L, 5 g/L, 10 g/L, 15 g/L, 20 g/L, 25 g/L, 30 g/L, 35 g/L, 40 g/L, 45 g/L, 50 g/L, or greater; acetone at a concentration greater than about 0.1 g/L, e.g., greater than about 1 g/L, 5 g/L, 10 g/L, 15 g/L, 20 g/L, 25 g/L, 30 g/L, 35 g/L, 40 g/L, 45 g/L, 50 g/L, or greater; or said carboxylic acid at a concentration greater than about 0.1 g/L, e.g., greater than about 1 g/L, 5 g/L, 10 g/L, 15 g/L, 20 g/L, 25 g/L, 30 g/L, 35 g/L, 40 g/L, 45 g/L, 50 g/L, or greater.

Further embodiments of the method of the second aspect are as described above, e.g., in embodiments of the method of the first aspect.

c. Method of the Third Aspect

According to a third aspect, provided is a method for producing butanol comprising (i) fermenting a fermentation medium comprising liquefied corn with a butanol producing organism to form a broth comprising butanol, a coproduct selected from a group consisting of ethanol, acetone and combinations thereof, at least one carboxylic acid and solids; (ii) separating wet solids from said broth to form a low-solids broth; (iii) contacting said low-solids broth with an extractant to form an extract and a raffinate, wherein said extract comprises said extractant, butanol, water, said coproduct and wherein said raffinate comprises said carboxylic acid; (iv) separating said extract from said raffinate; (v) separating extractant from at least a fraction of said extract to form separated extractant, a butanol-rich organic solution comprising said coproduct, and butanol comprising second aqueous solution; (vi) contacting at least a fraction of said second aqueous solution with said separated wet solids to form a mixture and separating butanol from said mixture to form a butanol-depleted residue and a first butanol stream; and (vii) distilling said butanol-rich organic solution to form refined butanol and separated coproduct; wherein; (a) extractant boiling point at atmospheric pressure is under 20° C.; (b) extractant Hansen solubility parameter polarity component is in the range between 2 MPa$^{0.5}$ and 8 MPa$^{0.5}$; and (c) extractant Hansen solubility parameter H-bond component is in the range between 2 MPa$^{0.5}$ and 8 MPa$^{0.5}$; and (d) extractant to broth ratio in said contacting is selected so that the formed extract comprises at least about 40%, e.g., at least about 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, of the butanol in the broth.

According to an embodiment, the fermentation medium of the third aspect comprises liquefied corn, a nitrogen source and nutrients. According to various embodiments, it also comprises at least one carboxylic acid, extractant, ethanol, acetone or combinations thereof. According to an embodiment, recycled raffinate is used to form said fermentation medium. In varying embodiments, the raffinate is not further sterilized prior to being recycled to form the fermentation medium. According to an embodiment, said liquefied corn is combined with recycled raffinate (as such or after modification) to form said fermentation medium.

The method of the third aspect comprises fermenting said medium with a butanol producing organism to form a broth comprising butanol, said coproduct, at least one carboxylic acid and optionally also a carbon source, a nitrogen source, an extractant and combinations thereof. According to an embodiment, said fermentation medium is inoculated with said organism.

According to an embodiment, said organism is characterized by resistance to (e.g., ability or capability to be viable in) extractant at a concentration of at least about 1.0 g/L, e.g., at least about 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, or 95 g/L, and up to about 100 g/L.

According to an embodiment, said organism is resistant to extractant concentration greater than 1.0 g/L, to butanol concentration greater than 1.0 g/L, to ethanol concentration greater than 1.0 g/L, to acetone concentration greater than 1.0 g/L, and to combinations thereof.

Suitable organisms are as described above (e.g. in embodiments for the method of the first aspect) and herein. According to an embodiment, suitable bacteria can include those that are capable of butanol production, e.g., including without limitation *Firmicutes*, e.g., including without limitation *Clostridia*. Illustrative *Clostridia* include, e.g., *Clostridium* and *Eubacterium*. Illustrative *Clostridium* of these include without limitation, *Clostridium butyricum, Clostridium acetobutylicum, Clostridium saccharoperbutylacetonicum, Clostridium saccharobutylicum, Clostridium beijerickii, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum, Clostridium autoethanogenum*. Illustrative *Eubacterium* include *Eubacterium limosum*.

According to an embodiment, said carboxylic acid is selected from a group consisting of acetic acid, butyric acid and lactic acid.

According to an embodiment, during contacting with the extractant, the low-solids broth is maintained at a pH greater than about 6, e.g. in the range between about 6 and about 10, e.g., between about 6 and about 9, or between about 6.1 and about 8 or between about 7 and about 9, e.g., between about 8 and about 9. According to an embodiment, the method of the first embodiment comprises checking the pH of said low-solids broth and if under 6, contacting with a base to adjust it to above 6. According to an embodiment, said contacting with a base comprises adding a base to the broth, e.g. adding NaOH. Alternatively or additionally, said contacting comprises contacting with a basic ion-exchanger, e.g. one carrying an amine function or carrying a weak acid function in a salt form.

The method of the third aspect comprises separating wet solids from said broth prior to said contacting to form a low-solids broth. Any form of solids separation is suitable. According to an embodiment, said separation uses at least one of centrifugation and filtration.

The method of the third aspect comprises contacting said low-solids broth with an extractant to form an extract and a raffinate, wherein said extract comprises said extractant, butanol, water, said coproduct and wherein said raffinate comprises said carboxylic acid and optionally a carbon source, a nitrogen source and extractant. Said contacting is also referred to in the following as extracting. In a following step, said extract is separated from said raffinate.

The extractant used in the method of the third aspect has a boiling point at atmospheric pressure under 20° C. Its Hansen solubility parameter polarity component is in the range between 2 MPa$^{0.5}$ and 8 MPa$^{0.5}$ and its Hansen solubility parameter H-bond component is in the range between 2 MPa$^{0.5}$ and 8 MPa$^{0.5}$.

According to an embodiment said extractant comprises an ether selected from the group consisting of dimethyl ether (DME), methyl ethyl ether (methoxyethane), and mixtures thereof. According to an embodiment said extractant is selected from the group consisting of dimethyl ether (DME), methyl ethyl ether, and mixtures thereof. According to an embodiment, at least about 95%, at least about 98% or at least about 99% of the extractant is selected from the group consisting of dimethyl ether (DME), methyl ethyl ether (methoxyethane), and mixtures thereof.

In various embodiments, said contacting is conducted at a temperature in the range of about 20° C. to about 35° C., for example, about 20° C., 21° C., 22° C., 23° C., 24° C., 25° C., 26° C., 27° C., 28° C., 29° C., 30° C., 31° C., 32° C., 33° C., 34° C. or 35° C. In various embodiments, contacting is conducted at a fermentation temperature. For example, for certain organisms, fermentation temperature is in the range of about 35° C. to about 40° C., for example at a temperature of about 35° C., 36° C., 37° C., 38° C., 39° C. or 40° C.

In various embodiments, said contacting is conducted at above about 85 psi (5.9 bar; 5.8 atm) and below 145 psi (10 bar; 9.87 atm), for example, about 85 psi (5.9 bar; 5.8 atm); 87 psi (6 bar; 5.9 atm); 102 psi (7 bar; 6.9 atm); 116 psi (8 bar; 7.9 atm); 131 psi (9 bar; 8.9 atm); or 145 psi (10 bar; 9.87 atm).

Any form of contacting is suitable. Any form of extract separation from the raffinate is suitable. According to an embodiment, said contacting comprises multiple-stage contacting, e.g., having between 2 and 40 stages, e.g., between 2 and 30, 2 and 20, 2 and 10 or 2 and 6 stages. According to an embodiment, contacting is conducted in a counter-current mode. According to various embodiments, contacting and separation are conducted in a column operation or in a set of mixer settlers.

According to varying embodiments, the flux ratio of extractant to broth is in the range of from about 0.5 to about 20, e.g., about 0.5, 1, 2, 3, 4, 5, 6, 7, 8, 9, 10, 11, 12, 13, 14, 15, 16, 17, 18, 19, or 20. In some embodiments, the flux ratio of extractant to aqueous solution is in the range of from about 1 to about 3.

According to a first embodiment of said third aspect, the extractant to low-solids broth flux ratio is selected so that at least about 70%, e.g., at least about 75%, 80%, 85%, 90%, 95%, 96%, 97%, 98%, 99%, 99.5%, or more, of both the butanol and said coproduct are extracted. According to said embodiment, said raffinate comprises less than about 30%, e.g., less than about 25%, 20%, 15%, 10%, or less, of both the butanol and said coproduct.

According to a second embodiment of the third aspect, the selected flux ratio is sufficient for high butanol extraction yield, but smaller than required for such high yield of extracting components other than butanol. As a result, the fraction of the broth butanol in said extract (butanol extraction yield) is greater than the fraction of the broth other component in said extract (extraction yield of the other component).

According to said second embodiment, said broth comprises ethanol and butanol extraction yield is greater than ethanol extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to an embodiment, said broth comprises acetone and butanol extraction yield is greater than acetone extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more. According to said second embodiment, said extract comprises less than about 10%, e.g., less than about 9%, 8%, 7%, 6%, 5%, 4%, 3%, 2%, 1% or 0.5% of the carboxylic acid in said broth, i.e. carboxylic acid extraction yield is less than about 10%, e.g., less than about 9%, 8%, 7%, 6%, 5%, 4%, 3%, 2%, 1% or 0.5%. Additionally or alternatively, the carbon source extraction yield is less than about 10%, e.g., less than about 9%, 8%, 7%, 6%, 5%, 4%, 3%, 2%, 1% or 0.5%. Additionally or alternatively, the nitrogen source extraction yield is less than about 10%, e.g., less than about 9%, 8%, 7%, 6%, 5%, 4%, 3%, 2%, 1% or 0.5%. Additionally or alternatively, the extraction yield of other nutrient, e.g. vitamins and minerals, is less than about 10%, e.g., less than about 9%, 8%, 7%, 6%, 5%, 4%, 3%, 2%, 1% or 0.5%.

According to said second embodiment, the raffinate contains only a small fraction of the broth original butanol content, e.g. less than about 15%, e.g., less than about 10%, 5%, or less, of the original butanol content, but large fractions of the other broth components, e.g. more than about 30%, e.g., more than about 40%, 50%, 60%, 70%, 80%, or more, of the ethanol, more than about 30%, e.g., more than about 40%, 50%, 60%, 70%, 80%, or more, of the acetone, more than about 50%, e.g., more than about 60%, 70%, 80%, or more, of the carboxylic acid, more than 50%, e.g., more than about 60%, 70%, 80%, or more, of the carbon source, more than about 50%, e.g., more than about 60%, 70%, 80%, or more, of the nitrogen source, more than about 50% of other nutrients and combinations thereof. According to said second embodiment, said raffinate, as such, or after pretreatment, is recycled to form said fermentation medium in a following cycle. In varying embodiments, the raffinate is not further sterilized prior to being recycled to form the fermentation medium.

The method of the third aspect comprises separating extractant from at least a fraction of said extract to form separated extractant, a butanol-rich organic solution comprising said coproduct, and butanol-comprising second aqueous solution.

According to an embodiment, said extractant separation from the extract comprises application of heat and, optionally, pressure reduction, whereby extractant evaporates. Hence, according to an embodiment, both contacting the extractant and extract separation from the raffinate are conducted at super-atmospheric pressure, followed by application of heat and, optionally, reducing the pressure of the extract whereby the extractant evaporates. According to an embodiment, the vaporized extractant is separated and then condensed to reform the extractant for contacting in the following cycle. According to an embodiment, said vaporizing and said condensing are driven by a refrigerant circuit.

Said butanol-rich organic solution comprising, according to an embodiment, at least about 35%, e.g., at least about 40%, 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, butanol. According to an embodiment, this butanol-rich organic solution is separated from said second aqueous solution, by known means, such as decanting in a suitable decanter. According to the method of the third aspect said butanol-rich organic solution is distilled to form refined butanol and separated coproduct. The high butanol concentration in that organic solution saves on energy costs for generating said refined butanol.

According to an embodiment, said coproduct is ethanol and distilling said separated butanol-rich organic solution forms refined butanol and separated ethanol. According to an embodiment, said coproduct is acetone and distilling said separated butanol-rich organic solution forms refined butanol and separated acetone. According to an embodiment, said coproduct comprises both ethanol and acetone and distilling said separated butanol-rich organic solution forms refined butanol, separated ethanol and separated acetone.

According to an embodiment, butanol concentration in said butanol comprising second aqueous solution is in the range between about 10 g/L and about 250 g/L, e.g., at least about 10 g/L, 20 g/L, 30 g/L, 40 g/L or 50 g/L to about 150 g/L, 175 g/L, 200 g/L, 225 g/L, or 250 g/L. According to an embodiment, said butanol comprising second aqueous solution still comprises a significant fraction of the broth butanol, e.g. more than about 20%, e.g., more than about 25%, 30%, 35%, 40%, 45%, 50%, or more, of the broth butanol, and said embodiment comprises separating butanol from at least a fraction of said second aqueous solution to form a first butanol stream and a butanol-depleted residue. According to an embodiment, butanol is separated from at least two different fractions of said second aqueous solution and said separation differs between the fractions. According to an embodiment, at least one of those fractions is combined with another process stream before said butanol separation.

The method of the third aspect comprises contacting said separated wet solids with at least a fraction of said second aqueous solution to form a mixture and separating butanol from said mixture to form a first butanol stream and a butanol-depleted residue. According to an embodiment, separating butanol from said mixture (typically a slurry of the solids in said second aqueous solution) comprises distillation forming a butanol-comprising vapor phase (the first butanol stream) and a butanol-depleted solid or suspension (the butanol-depleted residue).

According to an embodiment, said second aqueous solution comprises said coproduct and said first butanol stream also comprises said coproduct. According to an embodiment, said first butanol stream is combined with at least one other butanol-comprising stream to form a combined stream for further processing. According to an embodiment, said first butanol stream is combined with the extract, with a stream formed in distilling said butanol-rich organic solution or both. According to an embodiment, said combined stream is split into said butanol-rich organic solution and said second aqueous solution.

According to an embodiment, said solids-comprising butanol-depleted residue is used as an ingredient in animal feed. According to an embodiment, the third aspect of the invention provides an animal feed composition comprising at least a fraction of said butanol-depleted residue. According to an embodiment, the third aspect of the invention further provides a method for the production of said animal feed composition, comprising at least one of treating said butanol-depleted residue with an enzyme having phytase activity and drying.

According to an embodiment, butanol separation from at least a fraction of said second aqueous solution comprises at least one of distillation and extraction. According to an embodiment, said fraction of the second aqueous solution is combined with another process stream before said at least one of distillation and extraction. According to an embodiment, said fraction of the second aqueous solution is combined with the low-solids broth prior to said contacting with the extractant. Additionally or alternatively, said at least a fraction of said second aqueous solution is contacted with at least a fraction of said extract to form a butanol-depleted solution and a butanol enriched extract.

Hence, according to an embodiment, extraction is conducted in a column equipped with at least three input ports, first one at the bottom or near the bottom, a second one at the top or near the top and a third one between the two, e.g. at the upper half of the column. The column also has at least two output ports, a first one at the bottom or near the bottom and second one at the top or near the top and above the second input port. The extractant is fed to the column through the first input port, flows upwards and exits through the second output port. The fraction of the second aqueous solution is fed through the second input port and the low-solids broth through the third input port and the combined formed raffinate exits via the first output port. Alternatively, extraction is conducted through a battery of mixer-settlers with three input ports and two output ports, and similarly to the column case, the extractant and the second aqueous solution are introduced at the two ends and the low-solids broth is introduced along the way. Extraction according to these embodiments generates an extract with butanol/water ratio greater than that formed on extracting a mixture of the low-solids broth and the second aqueous solution.

According to various embodiments, said fermentation medium comprises ethanol at a concentration greater than 0.1 g/L; acetone at a concentration of 0.1 g/L or greater than 0.1 g/L; or said carboxylic acid at a concentration greater than 0.1 g/L.

Further embodiments of the method of the third aspect are as described above, e.g., in embodiments of the method of the first aspect.

d. Method of the Fourth Aspect

According to a fourth aspect, provided is a method for producing butanol comprising: (i) fermenting a medium comprising a carbon source (e.g., carbohydrate composition) and a nitrogen source with a butanol producing organism that is viable in a broth comprising a concentration of at least about 1.0 g/L extractant to form a broth comprising butanol (e.g., n-butanol, iso-butanol and/or sec-butanol) and at least one carboxylic acid; (ii) maintaining the pH of said low-solids broth at a pH above about 6; (iii) contacting said broth with an extractant to form an aqueous raffinate comprising said carboxylic acid and an extract comprising butanol and water; (iv) separating extractant from at least a fraction of said extract to form separated extractant, a butanol-rich organic phase, and butanol-comprising second aqueous phase; and (v) distilling said butanol-rich organic phase to form refined butanol; wherein (a) extractant boiling point at atmospheric pressure is under 20° C.; (b) extractant Hansen solubility parameter polarity component is in the range between 2 $MPa^{0.5}$ and 8 $MPa^{0.5}$; and (c) extractant Hansen solubility parameter H-bond component is in the range between 2 $MPa^{0.5}$ and 8 $MPa^{0.5}$.

According to various embodiments, said organism is a *Firmicutes*, said organism is a *Clostridia* and said organism is a *Eubacterium*. According to a related embodiment, said *Eubacterium* is a *Eubacterium limosum*. Alternatively, said organism is a *Clostridium*. According to a related embodiment, said *Clostridium* selected from the group consisting of *Clostridium butyricum, Clostridium acetobutylicum, Clostridium saccharoperbutylacetonicum, Clostridium beijerickii., Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum* and *Clostridium autoethanogenum*.

According to an embodiment, said broth comprises ethanol, said organic phase comprises ethanol and said distilling said butanol-rich organic phase further forms separated ethanol.

According to an embodiment, said broth comprises acetone, said organic phase comprises acetone and said distilling said butanol-rich organic phase further forms separated acetone.

According to an embodiment, said organism is modified to eliminate ethanol production. Alternatively or additionally, said organism is modified to eliminate acetone production.

Further embodiments of the method of the fourth aspect are as described above, e.g., in embodiments of the method of the first aspect.

e. Method of the Fifth Aspect

According to a fifth aspect, provided is a butanol composition comprising at least 40 wt. %, e.g., at least about 45 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %, 65 wt. %, 70 wt. %, 75 wt. %, 80 wt. %, 85 wt. %, 90 wt. %, 95 wt. %, 96 wt. %, 97 wt. %, 98 wt. %, 99 wt. %, 99.5 wt. %, or more, butanol and at least 100 ppb, e.g., at least about 1000 ppb, 1 ppm, 10 ppm, or 100 ppm of extractant, e.g., dimethyl ether, methyl ethyl ether, or a mixture thereof.

According to various embodiments, said composition comprises at least one of water, ethanol and acetone. According to an embodiment, the water content of the composition is in the range between 0.001% and 10%. According to an embodiment, the ethanol content of the composition is in the range between 0.001% and 10%. According to an embodiment, the acetone content of the composition is in the range between 0.001% and 10%.

Any known analytical method is suitable for determining the extractant (e.g., dimethyl ether, methyl ethyl ether, or a mixture thereof) content of the composition in a range of 10 ppb to 100 ppm e.g., using headspace gas chromography or quadrupole mass spectroscopy. In case extractant (e.g., dimethyl ether, methyl ethyl ether, or a mixture thereof) content of the composition is small, larger amounts of the composition are treated to separate DME therefrom, e.g. by stripping or head space gas chromatograph analysis.

Further embodiments of the method of the fifth aspect are as described above, e.g., in embodiments of the method of the first aspect.

f. Method of the Sixth Aspect

According to a sixth aspect, provided is a method for producing a fermentation product and at least one fermentation coproduct comprising: (i) combining a carbon source with a first aqueous solution comprising a fermentation coproduct and extractant to form a fermentation medium; (ii) fermenting said medium with an organism to form a broth comprising a product, said coproduct, and extractant; (iii) contacting said broth with an extractant to form an extract and a raffinate, wherein said extract comprises said extractant, said product and water and wherein said raffinate comprises said coproduct and extractant; (iv) separating said extract from said raffinate; (v) separating extractant from at least a fraction of said extract to form separated extractant and extractant-depleted extract; (iv) separating product from at least a fraction of said extractant-depleted extract to form a product stream; and (vii) repeating steps (i) to (vi), wherein said first aqueous solution comprises said raffinate and wherein said separated extractant is used in said contacting; wherein (a) extractant boiling point at atmospheric pressure is under 20° C.; (b) extractant Hansen solubility parameter polarity component is in the range between 2 MPa$^{0.5}$ and 8 MPa$^{0.5}$; (c) extractant Hansen solubility parameter H-bond component is in the range between 2 MPa$^{0.5}$ and 8 MPa$^{0.5}$; (d) extractant to broth ratio in said contacting is selected so that the formed extract comprises at least 40%, e.g., at least about 45%, 50%, 51%, 52%, 53%, 54%, 55%, 56%, 57%, 58%, 59%, 60%, 65%, 70%, 75%, 80%, 85%, 90%, 95%, 96%, 97%, 98%, 99%, 99.5%, or more, of the butanol in the broth; and (e) said coproduct is selected from a group consisting of carboxylic acids and biomolecules characterized by solubility parameter greater than that of said product.

According to an embodiment, said product is one or more C3-C9 alcohols. According to an embodiment said one or more C3-C9 alcohols are selected from a propanol, a butanol, a pentanol, a hexanol, a heptanol, an octanol, and a nonanol. According to an embodiment said alcohol is propanol. According to a related embodiment, said propanol is selected from the group consisting of 1-propanol and 2-propanol. According to an embodiment said alcohol is butanol. According to a related embodiment said butanol is selected from the group consisting of 1-butanol, 2-butanol, tert-butanol (2-methyl-2-propanol), and iso-butanol (2-methyl-1-propanol). According to an embodiment said alcohol is pentanol. According to a related embodiment said pentanol is selected from the group consisting of 1-pentanol, 2-pentanol, 3-pentanol, 2-methyl-1-butanol, 3-methyl-1-butanol, 2-methyl-2-butanol, 3-methyl-2-butanol, and 2,2-dimethyl-1-propanol. According to an embodiment said alcohol is hexanol. According to a related embodiment said hexanol is selected from the group consisting of 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, and 2-ethyl-1-butanol. According to a related embodiment said heptanol is selected from all isomers of heptanol. According to a related embodiment said octanol is selected from all isomers of octanol. According to a related embodiment said nonanol is selected from all isomers of nonanol.

According to an embodiment, said product is one or more C3-C6 carboxylic acids or dicarboxylic acids. According to a related embodiment, said one or more C3-C6 carboxylic acids or dicarboxylic acids are selected from the group consisting of propionic acid, lactic acid, malonic acid, fumaric acid, succinic acid, itaconic acid, levulinic acid, hexanoic acid, and 3-hydroxybutyric acid.

According to an embodiment, said product is one or more one or more C2-C18 dicarboxylic acids. According to a related embodiment, said one or more C2-C18 dicarboxylic acids are selected from the group consisting of oxalic, propanedioic, butanedioic, pentanedioic, hexanedioic, heptanedioic, octanedioic, nonanedioic, decanedioic, undecanedioic, and dodecanedioic (DDDA).

According to an embodiment, said product is one or one or more C8-C18 fatty alcohols. According to a related embodiment, said one or more C8-C18 fatty alcohols are selected from the group consisting of capryl alcohol (1-octanol), 2-ethyl hexanol, pelargonic alcohol (1-nonanol), capric alcohol (1-decanol, decyl alcohol), undecyl alcohol (1 undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol) and stearyl alcohol (1-octadecanol).

According to an embodiment, said product is one or one or more butanediols. According to a related embodiment, said one or more butanediols are selected from 1,4-butanediol and 2,3-butanediol.

According to an embodiment, said product is one or one or more butadienes. According to a related embodiment, said one or more butadienes are selected from the group consisting of butadiene and 2-methyl-1,3-butadiene (isoprene).

According to an embodiment, said product is one or one or more furfural. According to a related embodiment, said one or more furfurals are selected from the group consisting of furfural and hydroxymethylfurfural (5-(hydroxymethyl)-2-furaldehyde).

According to an embodiment, said product is acetoin and/or furan.

According to various embodiments, said product has a solubility in water of less than about 15 wt. % at 25° C.; has a carbon atom number to hydroxyl group ratio of 3 or greater; has a melting point of 100° C. or less.

According to an embodiment, said product is butanol and said coproduct is selected from a group consisting of ethanol, acetone, a carboxylic acid and their combinations. According to an embodiment, said product is butanol and said method comprises distilling said product rich organic solution to form refined butanol. According to an embodiment, said product is butanol and said extract comprises said coproduct. According to a related embodiment, said coproduct comprises ethanol and the method comprises distilling said product rich organic solution to form refined butanol and separated ethanol. According to another related embodiment, said coproduct comprises acetone and the method comprises distilling said product rich organic solution to form refined butanol and separated acetone. According to still another related embodiment, said coproduct comprises ethanol and acetone and the method comprises distilling said product rich organic solution to form refined butanol, separated ethanol and separated acetone.

According to an embodiment, said product is propionic acid and said coproduct is acetic acid.

According to an embodiment, said product is gamma-butyrolactone and said coproduct is 1,4-butanediol.

According to an embodiment, said product is butanol and said coproduct is 1,3-propanediol.

According to an embodiment, said product is hexanol and said coproduct is acetic acid.

According to an embodiment, said coproduct is acetic acid.

According to an embodiment, said product is selected from the group consisting of carboxylic acids, dicarboxylic acid and fatty acids and said broth is maintained at pH of under about 5.

According to an embodiment, said coproduct is selected from the group consisting of carboxylic acids and said broth is maintained at pH of above about 6.

In varying embodiments, the coproduct of the sixth aspect is selected from a group consisting of carboxylic acids and biomolecules characterized by solubility parameter greater than that of said product. According to an embodiment, the solubility parameter of said coproduct is greater than that of the product by at least about $0.5$ $MPa^{0.5}$, e.g., at least about $0.75$ $MPa^{0.5}$, at least about $1.0$ $MPa^{0.5}$, $1.5$ $MPa^{0.5}$, $2.0$ $MPa^{0.5}$, $2.5$ $MPa^{0.5}$, $3.0$ $MPa^{0.5}$, $3.5$ $MPa^{0.5}$, $4.0$ $MPa^{0.5}$, $4.5$ $MPa^{0.5}$, $5.0$ $MPa^{0.5}$, $5.5$ $MPa^{0.5}$, $6.0$ $MPa^{0.5}$, $6.5$ $MPa^{0.5}$, $7.0$ $MPa^{0.5}$, $7.5$ $MPa^{0.5}$ or $8.0$ $MPa^{0.5}$.

According to an embodiment, said coproduct is assimilated. According to a related product embodiment, said coproduct is assimilated to at least one of ethanol, acetone and butanol.

According to an embodiment, said first aqueous solution comprises at least one of a carboxylic acid, a carbon source (e.g., carbohydrate) and a nitrogen source. According to an embodiment, said first aqueous solution comprises at least 1 g/L carbohydrate. According to an embodiment, said first aqueous solution comprises less than 500 g/L carbohydrate. According to an embodiment, said first aqueous solution comprises at least 0.1 g/L carboxylic acid. According to an embodiment, said first aqueous solution comprises less than 150 g/L carboxylic acid.

According to an embodiment, said broth comprises at least one of a carboxylic acid, a carbon source (e.g., carbohydrate) and a nitrogen source. According to an embodiment, said broth comprises at least 1 g/L carbohydrate. According to an embodiment, said broth comprises less than 500 g/L carbohydrate. According to an embodiment, said broth comprises at least 0.1 g/L carboxylic acid. According to an embodiment, said broth comprises less than 150 g/L carboxylic acid.

According to an embodiment, said raffinate comprises at least one of a carboxylic acid, a carbon source (e.g., carbohydrate) and a nitrogen source. According to an embodiment, said raffinate comprises at least 1 g/L carbohydrate. According to an embodiment, said raffinate comprises less than 500 g/L carbohydrate. According to an embodiment, said raffinate comprises at least 0.1 g/L carboxylic acid. According to an embodiment, said raffinate comprises less than 150 g/L carboxylic acid.

According to an embodiment, said extract comprises said coproduct.

According to an embodiment, said extractant-depleted extract comprises a product-rich organic solution and a product comprising second aqueous solution. According to a related embodiment, the method comprises separating product from at least a fraction of said second aqueous solution to form a first product stream and a product-depleted residue.

According to an embodiment, said carbon source comprises liquefied corn, and the method further comprises separating wet solids from said broth prior to said contacting. According to a related embodiment, said extractant-depleted extract comprises a product rich organic solution and a product comprising second aqueous solution and said method comprises contacting said separated wet solids with a fraction of said second aqueous solution to form a mixture and separating product from said mixture to form product-depleted residue.

According to an embodiment, said organism is viable in a broth comprising extractant at a concentration of at least extractant at a concentration of at least about 1.0 g/L, e.g., at least about 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, or 95 g/L, and up to about 100 g/L.

According to various embodiments, said organism is a *Firmicutes*, said organism is a *Clostridia* and said organism is a *Eubacterium*. According to a related embodiment, said *Eubacterium* is a *Eubacterium limosum*. Alternatively, said organism is a *Clostridium*. According to a related embodiment, said *Clostridium* is selected from the group consisting of *Clostridium butyricum*, *Clostridium acetobutylicum*, *Clostridium saccharoperbutylacetonicum*, *Clostridium beijerickii.*, *Clostridium saccharobutylicum*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum* and *Clostridium autoethanogenum*.

According to an embodiment, said fermentation medium is inoculated with said organism.

According to an embodiment, said carboxylic acid is selected from a group consisting of acetic acid, butyric acid and lactic acid.

According to an embodiment, said extractant comprises an ether selected from the group consisting of dimethyl ether (DME), methyl ethyl ether (methoxyethane), and mixtures thereof.

According to an embodiment, at least a fraction of said second aqueous solution is contacted with at least a fraction of said extract to form a product-depleted solution and a product-enriched extract.

According to an embodiment said first aqueous solution comprises at least about 0.1 wt %, e.g., at least about 0.2 wt %, 0.3 wt %, 0.5 wt %, 0.6 wt %, 0.7 wt %, 0.8 wt %, 0.9 wt %, 1.0 wt %, 1.5 wt %, 2.0 wt %, or more, of said extractant.

According to an embodiment extractant to broth ratio in said contacting is selected so that the fraction of the broth product in said extract is greater than the fraction of the broth coproduct in said extract. According to an embodiment product extraction yield is greater than coproduct extraction yield by a factor of at least about 1.3, e.g., at least about 1.4, 1.5, 1.6, 1.7, 1.8, 1.9, 2.0, 2.5, 3.0, 3.5, 4.0, 4.5, 5.0 or more.

According to an embodiment said fermentation medium comprises coproduct at a concentration greater than about 0.1 g/L.

According to an embodiment said fermentation medium comprises carboxylic acid at a concentration greater than about 0.1 g/L.

According to an embodiment said separating extractant comprises vaporizing, said using said separated extractant in said contacting comprises condensing and wherein said vaporizing and said condensing are driven by a refrigerant circuit.

According to an embodiment, the sixth aspect of the invention further provides a method for the production of said animal feed composition, comprising at least one of treating said butanol-depleted residue with an enzyme having phytase activity and drying.

Further embodiments of the method of the sixth aspect are as described above, e.g., in embodiments of the method of the first aspect.

Example 1: Distribution Coefficients and Selectivities in Extraction of a Synthetic Solution with Dimethyl Ether A synthetic solution was prepared, containing 15 g/L butanol, 10 g/L acetone, 10 g/L ethanol and about 965 g/L water. A 50 g sample of the synthetic solution was mixed, at 35° C., in a glass pressure vessel with 50 g liquefied dimethyl ether (extractant). Mixing was continued until equilibrium was reached. After settling, two phases were observed, a lighter phase (extract) and a heavier phase (raffinate). These two phases were separated by decantation. Extractant was separated from the extract to form extractant-depleted extract and from the raffinate to form extractant-depleted raffinate. The extractant-depleted phases were analyzed using HPLC chromatography. The results were used to calculate the concentrations of the components in the extract and in the raffinate prior to extractant separation and therefrom the distribution coefficients (DC) and the selectivities. DC for butanol, acetone, ethanol and water were 2.86, 1.27, 0.74 and 0.13, respectively. These results show that the extractant highest selectivity is for butanol, with butanol/water selectivity, butanol/acetone selectivity and butanol/ethanol selectivity of 22, 2.3 and 3.9, respectively.

Example 2: Formation of a Fermentation Medium

Extractant-depleted raffinate from a previous production cycle was analyzed and was found to contain 4.7 g/L acetic acid, 12 g/L dextrose, 0.5 g/L butyric acid, 4.3 g/L ethanol, 0.5 g/L acetone, 0.7 g/L butanol, 0.5 g/L nitrogen and 2 g/L dimethyl ether. In a fermentor of 15 liter, 10.5 Kg of the extractant-depleted raffinate were mixed with 1 Kg of 60% dextrose solution and 65 g hydrolyzed yeast extract to form a fermentation medium. The composition of the fermentation medium was 4.3 g/L acetic acid, 61.2 g/L dextrose, 1 g/L nitrogen and 1.96 g/L dimethyl ether.

Example 3: Fermenting the Fermentation Medium

The fermentation medium of Example 2 was inoculated with a 10% (v/v) mid-exponential phase growing culture and fermentation was continued for 33 hours. The formed fermentation broth was analyzed and was found to contain 15.9 g/L butanol, 4.0 g/L acetone, 9.6 g/L ethanol, 4.1 g/L acetic acid, 1.6 g/L butyric acid, 1.9 g/L dextrose, 1 g/L nitrogen, 0.3 g/L cell mass, less than 0.1 g/L dimethyl ether and balance of water. These results indicate that the dimethyl ether in the broth did not inhibit fermentation. The yield of butanol, acetone and ethanol combined was 39 g per 100 g dextrose.

Example 4: Extraction of Fermentation Broth

A fermentation broth (pH of 7) was extracted with recycled liquefied dimethyl ether (the extractant). Extraction was conducted in a counter-current mode in an extraction column providing about 4 theoretical stages. Extraction pressure and temperature were 80 psi and 35° C., respectively. The broth was fed, without removing the cell content, near the top of the column at a flux of 10 L/h. The extractant was fed near the bottom of the column at a flux of 10 L/h. The light phase (extract) was collected at the top of the column and the heavy phase (raffinate) at its bottom. The composition of the broth was 4.0 g/L acetone, 2.7 g/L ethanol, 13.6 g/L butanol, 6.7 g/L acetic acid, 1.5 g/L butyric acid and 49.1 g/L glucose. Both extract and raffinate were treated for extractant separation by heating and flashing. Extractant separation formed dimethyl ether vapors, extractant-depleted extract and extractant-depleted raffinate. The extractant-depleted extract was analyzed and found to contain 145.6 g/L butanol, 13.7 g/L acetone, 12.3 g/L ethanol, 1.18 g/L acetic acid, 0.2 g/L butyric acid, 0 g/L glucose and the balance essentially water. The extractant-depleted raffinate was analyzed and was found to contain 0.6 g/L butanol, 0.6 g/L acetone, 0.9 g/L ethanol, 7.96 g/L acetic acid, 52.4 g/L dextrose, 1 g/L nitrogen and 10.4 g/L dimethyl ether. The pH of the extractant-depleted raffinate was 6.7. The extraction results are in good agreement with those in Example 1. Butanol extraction yield was 96.5%. The high butanol/water selectivity resulted in a high concentration of butanol in the extract, about 14.6%. That concentration is greater by a factor of 10.7 compared with that in the fermentation broth. Butanol/water ratio in the extract, approximately 0.2, was 2.5 times greater than that in the fermentation broth. The extraction yields for acetone, ethanol and carboxylic acids were 83.9%, 68.8% and 4%, respectively. The rest was found in the raffinate. Essentially all dextrose and nitrogen source components of the broth were left in the raffinate. The composition of the extractant-depleted raffinate is essentially the same as that used for the production of the fermentation broth in Example 2.

Example 5: Liquefaction of Dimethyl Ether

The vapors of dimethyl ether generated during extractant separation of the extract and of the raffinate of Example 4 were liquefied, via a combination of cooling and pressurizing, to form liquefied extractant. That liquefied extractant is suitable to be recycled to extraction as in Example 4.

Example 6: Recycle of the Extractant-Depleted Raffinate

About 85% of the extractant-depleted raffinate formed in Example 4 was used to prepare a new fermentation medium as in Example 2 and in the same fermentor. That fermentation medium was inoculated and fermented as in Example 3 to form a fermentation broth of essentially the same composition as in Example 3. That fermentation broth was extracted as in Example 4, in the same extraction column and at same conditions. The extractant used was the liquefied dimethyl ether of Example 5. The formed extract and raffinate were treated for extractant separation and analyzed. The results were essentially the same as those of Example 4.

Example 7: Decantation

The extractant-depleted extract of Example 4 spontaneously separated into two phases, a lighter one and a heavier one. The mixture was allowed to settle until two clear phases were observed. Those two phases were separated by decantation. The lighter phase to heavier phase mass weight ratio was about 0.2. The two phases were analyzed. The lighter phase contained 541.6 g/L butanol, 14.2 g/L acetone, 11.4 g/L ethanol, 3.3 g/L acetic acid, 0 g/L butyric acid, and 299 g/L water. The heavier phase contained 73.6 g/L butanol, 14.1 g/L acetone, 11.9 g/L ethanol, 0.8 g/L acetic acid, 0.19 g/L butyric acid and 877 g/L water.

These results show that extraction and decantation of the extract according to the method have brought butanol concentration from about 15 g/L in the broth to more than 540 g/L in the decanted light phase.

Example 8: Butanol Separation from Ethanol and Acetone

10 Kg of an extract, decanted light phase was distilled in a distillation column at 56° C. The vapor phase was collected and analyzed. It contained 791 g/L acetone, 0.001 g/L ethanol, trace amounts of butanol and trace amounts of water. The heavy phase contained <0.001 g/L acetone, 13.5 g/L ethanol, 1.1 g/L acetic acid, 0.2 g/L butyric acid, 564.0 g/L butanol and 287 g/L water. The heavy phase was further distilled in a distillation column at 78° C. The vapor phase was collected and analyzed. It contained 795 g/L ethanol and 29 g/L water. The resulting heavy phase from the second distillation contained <0.001 g/L ethanol, 572.2 g/L butanol, 1.1 g/L acetic acid, 0.2 g/L butyric acid and 293.6 g/L water. Concentrated byproducts streams of high purity were formed.

Example 9: Butanol Refining

That heavy phase of Example 8 resulting from the second distillation was allowed to settle until two clear phases were observed. The two phases were separated by decantation. The lighter phase to heavier phase mass ratio was 4.4. The two phases were analyzed. The lighter phase contained 670 g/L butanol, 3.3 g/L acetic acid, 0 g/L butyric acid, and 173.7 g/L water. The heavier phase contained 69.8 g/L butanol, 0.8 g/L acetic acid, 0.19 g/L butyric acid and 913.8 g/L water. The lighter phase was distilled at 114° C. to form a vapor phase containing 570 g/L butanol and 295 g/L water and heavy phase of 810 g/L butanol, 5.5 g/L acetic acid, 0 g/L butyric acid, and trace amounts of water. Fermentation produced butanol was separated at high yield, high concentration and high purity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing butanol comprising:
   (i) combining a carbon source with a first aqueous solution comprising at least one carboxylic acid, a carbon source, a nitrogen source and extractant to form a fermentation medium;
   (ii) fermenting said medium with a butanol producing organism to form a broth comprising butanol, said carboxylic acid, a carbon source, a nitrogen source and extractant;
   (iii) contacting said broth with an extractant to form an extract and a raffinate, wherein said extract comprises said extractant, butanol and water and wherein said raffinate comprises said carboxylic acid, a carbon source, a nitrogen source and extractant;
   (iv) separating said extract from said raffinate;
   (v) separating extractant from at least a fraction of said extract to form separated extractant and extractant-depleted extract;
   (vi) separating butanol from at least a fraction of said extractant-depleted extract to form a first butanol stream; and
   (vii) repeating steps (i) to (vi), wherein said first aqueous solution comprises said raffinate and wherein said separated extractant is used in said contacting;
   wherein
   a. extractant boiling point at atmospheric pressure is under 20° C.;
   b. extractant Hansen solubility parameter polarity component is in the range between 2 MPa$^{0.5}$ and 8 MPa$^{0.5}$;
   c. extractant Hansen solubility parameter H-bond component is in the range between 2 MPa$^{0.5}$ and 8 MPa$^{0.5}$; and
   d. extractant to broth ratio in said contacting is selected so that the formed extract comprises at least 51% of the butanol in the broth.

2. The method according to claim 1, wherein said extractant-depleted extract comprises a butanol-rich organic solution and a butanol-comprising second aqueous solution.

3. The method according to claim 1, wherein said organism is viable in a broth comprising extractant at a concentration of at least about 1.0 g/L.

4. The method according to claim 1, wherein said extractant is selected from the group consisting of dimethyl ether (DME), methyl ethyl ether, and mixtures thereof.

5. A method for producing a fermentation product and at least one fermentation coproduct comprising:
   (i) combining a carbon source with a first aqueous solution comprising a fermentation coproduct and extractant to form a fermentation medium;
   (ii) fermenting said medium with an organism to form a broth comprising a product, said coproduct, and extractant;
   (iii) contacting said broth with an extractant to form an extract and a raffinate, wherein said extract comprises said extractant, said product and water and wherein said raffinate comprises said coproduct and extractant;
   (iv) separating said extract from said raffinate;
   (v) separating extractant from at least a fraction of said extract to form separated extractant and extractant-depleted extract;
   (vi) separating product from at least a fraction of said extractant-depleted extract to form a product stream; and
   (vii) repeating steps (i) to (vi), wherein said first aqueous solution comprises said raffinate and wherein said separated extractant is used in said contacting;
   wherein
   a. extractant boiling point at atmospheric pressure is under 20° C.;
   b. extractant Hansen solubility parameter polarity component is in the range between 2 MPa$^{0.5}$ and 8 MPa$^{0.5}$;
   c. extractant Hansen solubility parameter H-bond component is in the range between 2 MPa$^{0.5}$ and 8 MPa$^{0.5}$;
   d. extractant to broth ratio in said contacting is selected so that the formed extract comprises at least 51% of the butanol in the broth; and
   e. said coproduct is selected from the group consisting of carboxylic acids and biomolecules characterized by a Hansen solubility parameter component greater than that of said product.

6. The method according to claim 5, wherein at least one of said first aqueous solution, said broth and said raffinate comprises at least one of a carboxylic acid, a carbon source and a nitrogen source.

7. The method according to claim 5, wherein said extract further comprises said coproduct.

8. The method according to claim 5, wherein said extractant-depleted extract comprises a product-rich organic solution and a product comprising second aqueous solution.

9. The method according to claim 5, wherein said organism is viable in a broth comprising extractant at a concentration of at least about 1.0 g/L.

10. The method according to claim 5, wherein said organism is selected from a *Firmicutes*, a *Clostridia*, a *Eubacterium* and a *Eubacterium limosum*.

11. The method according to claim 5, wherein said organism is a *Clostridium* selected from the group consisting of *Clostridium butyricum, Clostridium acetobutylicum, Clostridium saccharoperbutylacetonicum, Clostridium beijerickii, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum* and *Clostridium autoethanogenum*.

12. The method according to claim 5, further comprising maintaining the pH of the broth above about pH 6 during contacting with the extractant.

13. The method according to claim 5, wherein said extractant comprises at least one of dimethyl ether (DME), methyl ethyl ether, and mixtures thereof.

14. The method according to claim 5, wherein said first aqueous solution comprises at least 0.1 wt. % of said extractant.

15. The method according to claim 5, wherein said fermentation medium comprises coproduct at a concentration greater than about 0.1 g/L.

16. The method according to claim 5, wherein
(i) said product is butanol and said coproduct is selected from the group consisting of ethanol, acetone, a carboxylic acid and their combinations;
(ii) said product is propionic acid and said coproduct is acetic acid;
(iii) said product is gamma-butyrolactone and said coproduct is 1,4-butanediol;
(iv) said product is butanol and wherein said coproduct is iso-propanol;
(v) said product is hexanol and wherein said coproduct is acetic acid; or
(vi) said coproduct is acetic acid.

17. The method according to claim 5, wherein said coproduct is assimilated to at least one of ethanol, acetone and butanol.

18. The method according to claim 5, wherein the product or co-product comprises one or more biomolecules selected from acetic acid, C3-C5 carboxylic acids, C3-C5 dicarboxylic acids, C3-C18 dicarboxylic acids, C8-C18 fatty alcohols, gamma-butyrolactone, butanediols, butadienes, furfurals, furan and acetoin.

19. The method according to claim 5, wherein said product has a solubility in water of less than about 15 wt. % at 25° C., a carbon number to hydroxyl group ratio of 3 or greater or a melting point of 100° C. or less.

20. The method according to claim 5, wherein a Hansen solubility parameter of said coproduct is greater than that of the product by at least about 0.5 $MPa^{0.5}$.

* * * * *

UNITED STATES PATENT AND TRADEMARK OFFICE
CERTIFICATE OF CORRECTION

PATENT NO. : 9,790,523 B2
APPLICATION NO. : 15/123512
DATED : October 17, 2017
INVENTOR(S) : Bryan P. Tracy et al.

Page 1 of 1

It is certified that error appears in the above-identified patent and that said Letters Patent is hereby corrected as shown below:

On the Title Page

Page 2, References Cited, Other Publications, (Column 2, Line 7), please change "Engineeting" to -- Engineering --.

In the Claims

At Column 46, Line 59 (Claim 5, Line 32), please replace "butanol" with -- product --.

Signed and Sealed this
Eleventh Day of December, 2018

Andrei Iancu
*Director of the United States Patent and Trademark Office*